United States Patent
O'Loughlin et al.

(10) Patent No.: US 7,198,785 B2
(45) Date of Patent: Apr. 3, 2007

(54) SYSTEMS AND METHODS RELATED TO DEGRADATION OF UREMIC TOXINS

(75) Inventors: Jill A. O'Loughlin, Lincoln, MA (US); Jan Markus Bruder, Altena (DE); Michael J. Lysaght, East Greenwich, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 10/731,877

(22) Filed: Dec. 9, 2003

(65) Prior Publication Data

US 2005/0123529 A1 Jun. 9, 2005

(51) Int. Cl.
C12N 11/00 (2006.01)

(52) U.S. Cl. .................... 424/93.2; 424/93.1; 424/93.4; 424/94.2; 424/94.4; 424/94.6; 435/174; 435/175

(58) Field of Classification Search ................ 435/183, 435/189, 191, 195, 227, 228, 231; 424/451, 424/463, 93.1, 93.4
See application file for complete search history.

(56) References Cited

U.S. PATENT DOCUMENTS 3,954,678 A * 5/1976 Marquisee ............... 252/62.54

(Continued)

FOREIGN PATENT DOCUMENTS

WO   WO 97/26903 A   7/1997

(Continued)

OTHER PUBLICATIONS

Prakash et al, "In vitro and in vivo uric acid lowering by artificial cells containing microencapsulated genetically engineered *E. coli* DH5 cells," The International Journal of Artificial Organs, 2000, vol. 23, No. 7, pp. 429-435.*

(Continued)

*Primary Examiner*—Leon B. Lankford, Jr.
*Assistant Examiner*—Allison M. Ford
(74) *Attorney, Agent, or Firm*—Wolf, Greenfield & Sacks, P.C.

(57) ABSTRACT

The present invention generally relates to the treatment of uremic toxins in vivo using uremic toxin-treating enzymes, and/or cells capable of producing uremic toxin-treating enzymes or otherwise reacting with uremic toxins. Non-limiting examples of cases where the treatment of uremic toxins is desired include renal disease or dysfunction, gout, subjects receiving chemotherapy, or the like. In one aspect, the treatment includes an oral delivery composition able to reduce the blood concentration of one or more non-protein nitrogen compounds in vivo. The composition, in some cases, may comprise one, two, or more uremic toxin-treating enzymes, such as urease, uricase or creatininase. The oral delivery composition may be able to deliver the uremic toxin-treating enzymes, substantially undigested, to the intestines, where the enzymes can interact with uremic toxins transported to the intestines from the bloodstream. In another aspect, the treatment includes an oral delivery composition comprising a cell able to reduce the concentration of one or more uremic toxins in vivo. In some cases, the cell may be designed to overexpress one, two, or more uremic toxin-treating enzymes, such as urease, uricase or creatininase, for example, by transfecting the cell with a corresponding gene. In some embodiments, a species able to react with or otherwise sequester by-products of the uremic toxin-treating enzyme reactions may be included with the oral delivery composition. For example, if the by-product is ammonium, the species may be a sorbent able to adsorb ammonium, an enzyme able to react with the ammonium, or the like.

7 Claims, 8 Drawing Sheets

U.S. PATENT DOCUMENTS

| | | | |
|---|---|---|---|
| 4,022,833 A | | 5/1977 | Diana et al. |
| 4,022,883 A | * | 5/1977 | Setala ..................... 424/93.3 |
| 4,240,376 A | * | 12/1980 | Kominami et al. ......... 119/214 |
| 4,857,555 A | * | 8/1989 | Smith et al. ................ 514/563 |
| 5,627,065 A | * | 5/1997 | Yamamoto et al. ......... 435/228 |
| 5,728,562 A | * | 3/1998 | Shigyo et al. .............. 435/191 |
| 6,126,938 A | | 10/2000 | Guy et al. |
| 6,217,859 B1 | | 4/2001 | Chang et al. |
| 2001/0051150 A1 | * | 12/2001 | Ranganathan et al. ..... 424/93.4 |

FOREIGN PATENT DOCUMENTS

WO     WO 02/069922 A     9/2002

OTHER PUBLICATIONS

The On-line Medical Dictionary "Creatininase" Mar. 5, 2000, accessed Feb. 28, 2005 http://cancerweb.ncl.ac.uk/cgi-bin/omd?query=creatininase.*

The On-line Medical Dictionary "Creatinine" Sep. 27, 1997, accessed Feb. 28, 2005 http://cancerweb.nci.ac.uk.cgi-bin/omd?creatinine.*

The On-line Medical Dictionary "Uricase" Dec. 12, 1998, accessed Feb. 28, 2005 http://cancerweb.nci.ac.uk/cgi-bin/omd?uricase.*

The On-line Medical Dictionary "Allantoin" Oct. 9, 1997, accessed Feb. 28, 2005 http://cancerweb.nci.ac.uk/cgi-bin/omd?allantoin.*

The On-line Medical Dictionary "Urease" Oct. 9, 1997, accessed Feb. 28, 2005 http://cancerweb.nci.ac.uk/cgi-bin/omd?urease.*

Merriam-Webster Online Dictionary "Enteric" accessed Feb. 28, 2005 http://www.m-w.com/cgi-bin/dictionary?book=Dictionary&va=enteric.*

Sparks et al, Trans. Am. Soc. Artif. Org., 1972, vol. 18, pp. 458-464, 484.*

IUBMB Enzyme Nomenclature "EC 3.5.2 10" retrieved from http://www.chem.qmul.ac.uk/iubmb/enzyme/EC3/5/2/10.htm on Jul. 6, 2006.*

Davankov, Vadim, et al., "Polymeric adsorbent for removing toxic proteins from blood of patients with kidney failure," *Journal of Chromatography B*, 739 (2000) 73-80.

Friedman, Eli A., M.D., "Can Bacteria Be Trained to Do the Kidney's Work?" http://www.thedoctorwillseeyounow.com/articles/emerging_treatments/kidneyre...2003-10-15, pp. 1-4.

Gardner, D. L., et al., "An Orally Administered Microcapsule System for Treating Chronic Renal Failure Patients," *Applied Biochemistry and Biotechnology*, vol. 10, 1984, pp. 27-40, Received Nov. 1983; Accepted Dec. 1983.

Malchesky, Paul S., M.S., et al., "Biological reactors as artificial organs: Concept and preliminary in vitro study," *Cleveland Clinic Quarterly*, 42: 267-271, vol. 42, No. 3, Fall 1975.

O'Loughlin, J. A., et al., "Microencapsulated Enzymes for Enteral Removal of Uremic Toxins," *Blood Purification*, 2003; 21: 350-367, 21st Annual Meeting of the International Society of Blood Purification (ISBP), Uncasville, CT, Sep. 2003, (Abstract).

O'Loughlin, J. A., et al., "Degradation of Uremic Toxins With Free and Encapsulated Enzymes," Presented at the meeting of the American Society of Artificial and Internal organs (ASAIO), Washington, DC, Jun. 2004, (Absract).

O'Loughlin, J. A., et al., "Kinetics of Urea Degradation By Genetically Modified *E. coli*," Presented at the meeting of the American Society of Artificial and Internal organs (ASAIO), New York, NY, Jun. 2002, p. 194, (Abstract).

O'Loughlin, J. A., et al., "Encapsulation of Mammalian And Bacterial Cells," Presented at the meeting for the Materials Research Society (MRS), Boston, MA, Nov. 2001, p. 640, (Abstract).

O'Loughlin, J. A., et al., "Release Of Albumin From Alginate Microspheres," Presented at the meeting for the Proceedings of the Controlled Release Society, San Diego, CA, Jun. 2001, #6042, (Abstract).

O'Loughlin, J. A., et al., "Degradation of Uremic Toxins with Free and Encapsulated Enzymes," Presented at the meeting of the Controlled Release Society, Glasgow, Scotland, Jun. 2003, (Abstract).

Prakash, S., et al., "Microencapsulated genetically engineered live *E. coli* DH5 cells administered orally to maintain normal plasma urea level in uremic rats," *Nature medicine*, vol. 2, No. 8, Aug. 1996, pp. 883-887.

Ronco, Claudio, et al., First Clinical Experience with an Adjunctive Hemoperfusion Device Designed Specifically to Remove $B_2$-in Microglobulin in Hemodialysis, *Blood Purification*, 2001; 19: 260-263.

Setala, K., et al., "Bacterial enzymes in uremia management," *Kidney International*, vol. 13, Suppl. 8 (1978), pp. S-194-S-202.

Setala, K., et al., "Treating uremia with soil bacterial enzymes: further developments*," *Clinical Nephrology*, Vo. 11, No. 3—1979 (pp. 156-166).

Winchester, James F., et al., "Sorbent Augmented Dialysis: Minor Addition or Major Advance in Therapy?" *Blood Purification*, 2001; 19: 255-259.

Wolfe, E. A., et al., "Orally ingested microencapsulated urease and an adsorbent, zirconium phosphate, to remove urea in kidney failure," *The International Journal Of Artificial Organs*, vol. 10, No. 4, 1987, pp. 269-274.

Nishida, Y., et al., "Hypo Uricemic Effect After Oral Administration In Chickens Of Poly Ethylene Glycol Modified Uricase Entrapped In Liposomes," *Journal of Pharmacy and Pharmacology*, vol. 36, No. 5, 1984, pp. 354-355.

Sprandel, U., "Erythrocytes as carrier for therapeutic enzymes—an approach towards enzyme therapy of inborn errors of metabolism," *Bibliotheca haematologica*, 1985, No. 51, pp. 7-14.

Search report mailed Apr. 22, 2005 from International Application No. PCT/US2004/040580, filed Dec. 3, 2004.

* cited by examiner

SEQUENCE LISTING

```
<160> NUMBER OF SEQ ID NOS: 3

<210> SEQ ID NO 1
<211> LENGTH: 840
<212> TYPE: PRT
<213> ORGANISM: Canavalia ensiformis

<400> SEQUENCE: 1

Met Lys Leu Ser Pro Arg Glu Val Glu Lys Leu Gly Leu His Asn Ala
1               5                   10                  15

Gly Tyr Leu Ala Gln Lys Arg Leu Ala Arg Gly Val Arg Leu Asn Tyr
            20                  25                  30

Thr Glu Ala Val Ala Leu Ile Ala Ser Gln Ile Met Glu Tyr Ala Arg
        35                  40                  45

Asp Gly Glu Lys Thr Val Ala Gln Leu Met Cys Leu Gly Gln His Leu
    50                  55                  60

Leu Gly Arg Arg Gln Val Leu Pro Ala Val Pro His Leu Leu Asn Ala
65                  70                  75                  80

Val Gln Val Glu Ala Thr Phe Pro Asp Gly Thr Lys Leu Val Thr Val
                85                  90                  95

His Asp Pro Ile Ser Arg Glu Asn Gly Glu Leu Gln Glu Ala Leu Phe
            100                 105                 110

Gly Ser Leu Leu Pro Val Pro Ser Leu Asp Lys Phe Ala Glu Thr Lys
        115                 120                 125

Glu Asp Asn Arg Ile Pro Gly Glu Ile Leu Cys Glu Asp Glu Cys Leu
    130                 135                 140

Thr Leu Asn Ile Gly Arg Lys Ala Val Ile Leu Lys Val Thr Ser Lys
145                 150                 155                 160

Gly Asp Arg Pro Ile Gln Val Gly Ser His Tyr His Phe Ile Glu Val
                165                 170                 175

Asn Pro Tyr Leu Thr Phe Asp Arg Arg Lys Ala Tyr Gly Met Arg Leu
            180                 185                 190

Asn Ile Ala Ala Gly Thr Ala Val Arg Phe Glu Pro Gly Asp Cys Lys
        195                 200                 205

Ser Val Thr Leu Val Ser Ile Glu Gly Asn Lys Val Ile Arg Gly Gly
    210                 215                 220

Asn Ala Ile Ala Asp Gly Pro Val Asn Glu Thr Asn Leu Glu Ala Ala
225                 230                 235                 240

Met His Ala Val Arg Ser Lys Gly Phe Gly His Glu Glu Lys Asp
                245                 250                 255

Ala Ser Glu Gly Phe Thr Lys Glu Asp Pro Asn Cys Pro Phe Asn Thr
            260                 265                 270

Phe Ile His Arg Lys Glu Tyr Ala Asn Lys Tyr Gly Pro Thr Thr Gly
        275                 280                 285

Asp Lys Ile Arg Leu Gly Asp Thr Asn Leu Leu Ala Glu Ile Glu Lys
    290                 295                 300
```

-continued

```
Asp Tyr Ala Leu Tyr Gly Asp Glu Cys Val Phe Gly Gly Lys Val
305                 310                 315                 320

Ile Arg Asp Gly Met Gly Gln Ser Cys Gly His Pro Pro Ala Ile Ser
            325                 330                 335

Leu Asp Thr Val Ile Thr Asn Ala Val Ile Asp Tyr Thr Gly Ile
            340                 345                 350

Ile Lys Ala Asp Ile Gly Ile Lys Asp Gly Leu Ile Ala Ser Ile Gly
            355                 360                 365

Lys Ala Gly Asn Pro Asp Ile Met Asn Gly Val Phe Ser Asn Met Ile
370                 375                 380

Ile Gly Ala Asn Thr Glu Val Ile Ala Gly Glu Gly Leu Ile Val Thr
385                 390                 395                 400

Ala Gly Ala Ile Asp Cys His Val His Tyr Ile Cys Pro Gln Leu Val
            405                 410                 415

Tyr Glu Ala Ile Ser Ser Gly Ile Thr Thr Leu Val Gly Gly Gly Thr
            420                 425                 430

Gly Pro Ala Ala Gly Thr Arg Ala Thr Thr Cys Thr Pro Ser Pro Thr
            435                 440                 445

Gln Met Arg Leu Met Leu Gln Ser Thr Asp Leu Pro Leu Asn Phe
450                 455                 460

Gly Phe Thr Gly Lys Gly Ser Ser Ser Lys Pro Asp Glu Leu His Glu
465                 470                 475                 480

Ile Ile Lys Ala Gly Ala Met Gly Leu Lys Leu His Glu Asp Trp Gly
            485                 490                 495

Ser Thr Pro Ala Ala Ile Asp Asn Cys Leu Thr Ile Ala Glu His His
            500                 505                 510

Asp Ile Gln Ile Asn Ile His Thr Asp Thr Leu Asn Glu Ala Gly Phe
            515                 520                 525

Val Glu His Ser Ile Ala Ala Phe Lys Gly Arg Thr Ile His Thr Tyr
            530                 535                 540

His Ser Glu Gly Ala Gly Gly His Ala Pro Asp Ile Ile Lys Val
545                 550                 555                 560

Cys Gly Ile Lys Asn Val Leu Pro Ser Ser Thr Asn Pro Thr Arg Pro
            565                 570                 575

Leu Thr Ser Asn Thr Ile Asp Glu His Leu Asp Met Leu Met Val Cys
            580                 585                 590

His His Leu Asp Arg Glu Ile Pro Glu Asp Leu Ala Phe Ala His Ser
            595                 600                 605

Arg Ile Arg Lys Lys Thr Ile Ala Ala Glu Asp Val Leu Asn Asp Ile
            610                 615                 620

Gly Ala Ile Ser Ile Ser Ser Asp Ser Gln Ala Met Gly Arg Val
625                 630                 635                 640

Gly Glu Val Ile Ser Arg Thr Trp Gln Thr Ala Asp Lys Met Lys Ala
            645                 650                 655

Gln Thr Gly Pro Leu Lys Cys Asp Ser Ser Asp Asn Asp Asn Phe Arg
            660                 665                 670

Ile Arg Arg Tyr Ile Ala Lys Tyr Thr Ile Asn Pro Ala Ile Ala Asn
            675                 680                 685

Gly Phe Ser Gln Tyr Val Gly Ser Val Glu Val Gly Lys Leu Ala Asp
            690                 695                 700

Leu Val Met Trp Lys Pro Ser Phe Phe Gly Thr Lys Pro Glu Met Val
705                 710                 715                 720

Ile Lys Gly Gly Met Val Ala Trp Ala Asp Ile Gly Asp Pro Asn Ala
```

```
                  725                 730                 735
Ser Ile Pro Thr Pro Glu Pro Val Lys Met Arg Pro Met Tyr Gly Thr
                740                 745                 750

Leu Gly Lys Ala Gly Ala Leu Ser Ile Ala Phe Val Ser Lys Ala
            755                 760                 765

Ala Leu Asp Gln Arg Val Asn Val Leu Tyr Gly Leu Asn Lys Arg Val
        770                 775                 780

Glu Ala Val Ser Asn Val Arg Lys Leu Thr Lys Leu Asp Met Lys Leu
785                 790                 795                 800

Asn Asp Ala Leu Pro Glu Ile Thr Val Asp Pro Glu Ser Tyr Thr Val
                805                 810                 815

Lys Ala Asp Gly Lys Leu Leu Cys Val Ser Glu Ala Thr Thr Val Pro
            820                 825                 830

Leu Ser Arg Asn Tyr Phe Leu Phe
        835                 840

<210> SEQ ID NO 2
<211> LENGTH: 296
<212> TYPE: PRT
<213> ORGANISM: Schizosaccharomyces pombe

<400> SEQUENCE: 2

Met Ser Glu Thr Thr Tyr Val Lys Gln Cys Ala Tyr Gly Lys Thr Leu
1               5                   10                  15

Val Arg Phe Met Lys Lys Asp Ile Cys Pro Lys Thr Lys Thr His Thr
            20                  25                  30

Val Tyr Glu Met Asp Val Gln Ser Leu Leu Thr Gly Glu Leu Glu Glu
        35                  40                  45

Ser Tyr Thr Lys Ala Asp Asn Ser Ile Val Val Pro Thr Asp Thr Gln
    50                  55                  60

Lys Asn Thr Ile Tyr Val Phe Ala Lys Asn Asn Asp Val Ser Val Pro
65                  70                  75                  80

Glu Val Phe Ala Ala Lys Leu Ala Lys His Phe Val Asp Lys Tyr Lys
                85                  90                  95

His Ile His Gly Ala Ala Leu Asp Ile Thr Ile Thr Pro Trp Thr Arg
            100                 105                 110

Met Glu Val Gln Gly Lys Pro His Ser His Ser Phe Ile Arg Asn Pro
        115                 120                 125

Gly Glu Thr Arg Lys Thr His Val Val Phe Ser Glu Gly Lys Gly Phe
    130                 135                 140

Asp Val Val Ser Ser Leu Lys Asp Val Leu Val Leu Lys Ser Thr Gly
145                 150                 155                 160

Ser Gly Phe Thr Asn Phe His Lys Cys Glu Phe Thr Thr Leu Pro Glu
                165                 170                 175

Val Thr Asp Arg Ile Phe Ser Thr Ser Ile Asp Cys Asn Tyr Thr Phe
            180                 185                 190

Lys His Phe Asp Thr Phe Glu Glu Leu Ala Gly Phe Asp Phe Asn Ser
        195                 200                 205

Ile Tyr Glu Lys Val Lys Glu Ile Thr Leu Glu Thr Phe Ala Leu Asp
    210                 215                 220

Asp Ser Glu Ser Val Gln Ala Thr Met Tyr Lys Met Ala Asp Thr Ile
225                 230                 235                 240

Ile Asn Thr Tyr Pro Ala Ile Asn Glu Val Tyr Tyr Ala Leu Pro Asn
                245                 250                 255
```

-continued

```
Lys His Tyr Phe Glu Ile Asn Leu Ala Pro Phe Asn Ile Asp Asn Leu
            260                 265                 270

Gly Ser Asn Cys Ser Leu Tyr Gln Pro Gln Ala Tyr Pro Ser Gly Tyr
            275                 280                 285

Ile Thr Cys Thr Val Ala Arg Lys
            290                 295

<210> SEQ ID NO 3
<211> LENGTH: 258
<212> TYPE: PRT
<213> ORGANISM: Arthrobacter sp.

<400> SEQUENCE: 3

Met Lys His Leu Ile Ser Asn Met Thr Trp Asn Glu Tyr Gln Asp Lys
1               5                   10                  15

Val Asp Lys Gly Phe Leu Ile Leu Pro Val Gly Ser Thr Glu Gln His
            20                  25                  30

Gly Pro His Leu Pro Leu Gly Val Asp Ala Val Ile Ser Thr Gln Phe
        35                  40                  45

Ser Leu Ala Ile Ala Arg Glu Leu Asn Ala Ala Val Ala Pro Val Leu
    50                  55                  60

Ser Tyr Gly Tyr Lys Ser Leu Pro Ala Ser Gly Gly Pro Met Phe
65                  70                  75                  80

Pro Gly Thr Ile Asp Leu Lys Gly Ser Thr Leu Thr Ser Leu Val Tyr
                85                  90                  95

Asp Leu Leu Glu Glu Phe Ile Ala Asp Gly Trp Lys Lys Ile Leu Ile
                100                 105                 110

Phe Ser Ala His Phe Glu Asn Glu Ala Phe Leu Ser Glu Ala Cys Asp
            115                 120                 125

Leu Leu Leu Arg Asn Gln Lys Glu Glu Phe Pro Lys Val Leu Ile Cys
    130                 135                 140

Asn Trp Trp Asp Asn Leu Ser Ala Glu Thr Met Ser Lys Val Phe Asp
145                 150                 155                 160

Glu Val Arg Phe Pro Gly Trp Ala Leu Glu His Ala Ala Ile Ser Glu
                165                 170                 175

Thr Ser Leu Met Met His Phe Ser Pro Glu Leu Val Lys Glu Asp Leu
            180                 185                 190

Ile Thr Asp Glu Gly Val Asn Asn Pro Pro Thr Tyr Gln Ser Phe Pro
        195                 200                 205

Pro Ser Lys Thr Leu Ile Pro Ala Ser Gly Cys Leu His Ser Ala Tyr
    210                 215                 220

Ser Ser Ser Ala Glu Lys Gly Lys Leu Ile Ala Leu Asp Ala Thr Lys
225                 230                 235                 240

Asn Ile Val Ser Phe Leu Ile Lys Glu Phe Ser Leu Glu Met Val Pro
                245                 250                 255

Ile Glu
```

SYSTEMS AND METHODS RELATED TO DEGRADATION OF UREMIC TOXINS

FIELD OF INVENTION

The present invention generally relates to the treatment of disorders associated with uremic toxins in vivo and, in particular, to the treatment of disorders associated with uremic toxins in vivo using uremic toxin-treating enzymes, and/or cells capable of producing uremic toxin-treating enzymes or otherwise reacting with uremic toxins.

DISCUSSION OF RELATED ART

The principle excretory function of the kidney is to maintain fluid balance and excrete waste metabolites. Typical rates of fluid and solute removal (per 24 hours) are~1.5 L of water, ~20 g of urea, ~5 g of electrolytes, and ~6 g of other metabolites, such as uric acid or creatinine. During renal dysfunction or failure, e.g., in end stage renal disease patients, waste metabolites normally excreted in the urine are instead retained in the blood and body tissues, leading to a pathological state commonly known as uremia or uremic toxicity.

Urea is the predominant nitrogen waste product of dietary protein catabolism. Uric acid is a product of nucleic acid degradation. Creatinine typically results from muscular protein breakdown. These components are normally eliminated in the urine via the kidneys. These components are also commonly used as markers to monitor kidney dialysis and other similar treatments. Although these waste metabolites are relatively nontoxic when acting alone, they are part of a more complex uremic toxicity syndrome, in which toxicity may result from the combined effects of these metabolites. Patients with renal dysfunction or failure often experience uremia, and typically will require dialysis to avoid uremic toxicity syndrome.

There are currently ~325,000 dialysis patients in the United States and ~1.3 million patients worldwide, with a cost of about $70,000 per patient/year, which translates to an estimated overall cost for dialysis care of about $80 billion (2003 figures). The patient population has an annual growth rate of ~7%. Since the early 1970's, the full cost of dialysis treatment in the United States has been paid for by Medicare, regardless of patient age or need. Nevertheless, the U.S. has quite a high mortality rate: ~50% of patients die within 3 years. A recent study compared the expected remaining lifetime for patients with selected diseases versus controls (i.e., free of disease) for the U.S. resident population in 1990. Study participants (aged 45 to 54) free of disease had an expected remaining lifetime of thirty years, compared to ten years for colon cancer patients and seven years for end stage renal disease patients. In another age bracket that was surveyed (aged 55 to 64), study participants free of disease had an expected remaining lifetime of twenty-two years, compared to ten and five years remaining for colon cancer and end stage renal disease patients respectively. In addition, ~10% of patients electively withdraw from dialysis treatment and accept a form of suicide.

Dialysis treatments often interfere with normal activities of daily living, since it typically is required three times a week, for three to five hours per session. Blood access is usually by percutaneous needle puncture. Secondary medical complications of uremia often arise, most commonly hypotension, leading to nausea, and cramps, and the like. These complications may be resolved by a kidney transplant, although the transplant recipient must still endure daily immunosuppressant treatment. Transplantation as a treatment for renal failure is scarce, as only ~14,000 donor organs (in the U.S.) are available each year, and there are currently over 80,000 patients on the waiting list (2003 figures).

There is thus a need for improvement in the treatment of uremic toxins in vivo.

SUMMARY OF INVENTION

The present invention generally relates to the treatment of disorders associated with uremic toxins in vivo using uremic toxin-treating enzymes, and/or cells capable of producing uremic toxin-treating enzymes or otherwise reacting with uremic toxins. The subject matter of this invention involves, in some cases, interrelated products, alternative solutions to a particular problem, and/or a plurality of different uses of one or more systems and/or articles.

In one aspect, the present invention is an article. The article, in one set of embodiments, includes an oral delivery composition. In one embodiment, the oral delivery composition includes at least one of isolated uricase and isolated creatininase. In another embodiment, the oral delivery composition includes at least one cell transfected with at least one of a uricase gene and a creatininase gene. In yet another embodiment, the oral delivery composition includes at least one cell designed to overexpress at least one of uricase and creatininase. The oral delivery composition includes, in still another embodiment, at least one cell transfected with at least one of a urease gene, a uricase gene, and a creatininase gene, where the at least one cell is not $E.$ $coli$. In yet another embodiment, the oral delivery composition includes at least one cell able to reduce a blood concentration of at least one non-protein nitrogen compound in a subject when the oral delivery composition is ingested by the subject, where the at least one cell is not $E.$ $coli$. In still another embodiment, the oral delivery composition includes at least two isolated uremic enzymes. In some cases, the oral delivery composition may include a capsule. The capsule, in some embodiments, may include one or more of the above-described compositions.

In another aspect, the present invention defines a method. In one set of embodiments, the method includes administering, to a subject, an oral delivery composition comprising at least one of uricase and creatininase. The method, in another set of embodiments, includes administering, to a subject, an oral delivery composition comprising at least one cell transfected with at least one of a uricase gene and a creatininase gene. The method, in yet another set of embodiments, includes administering, to a subject, an oral delivery composition comprising at least one cell designed to overexpress at least one of uricase and creatininase. In still another set of embodiments, the method includes administering, to a subject, an oral delivery composition comprising at least one cell transfected with at least one of a urease gene, a uricase gene, and a creatininase gene, where the at least one cell is not $E.$ $coli$. The method, in yet another set of embodiments, includes administering, to a subject, an oral delivery composition comprising at least one cell able to reduce a blood concentration of at least one non-protein nitrogen compound in the subject when the oral delivery composition is ingested by the subject, where the at least one cell is not $E.$ $coli$. In another set of embodiments, the method includes administering at least one of isolated uricase and isolated creatininase to an intestine of a subject. The method includes, in still another set of embodiments, administering, to a subject, an oral delivery composition comprising at least two isolated uremic enzymes.

In another aspect, the present invention is directed to a method of making one or more of the embodiments described herein, for example, an oral delivery capsule. In yet another aspect, the present invention is directed to a method of using one or more of the embodiments described herein, for example, an oral delivery capsule. In still another aspect, the present invention is directed to a method of promoting one or more of the embodiments described herein, for example, an oral delivery capsule.

Other advantages and novel features of the invention will become apparent from the following detailed description of the various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
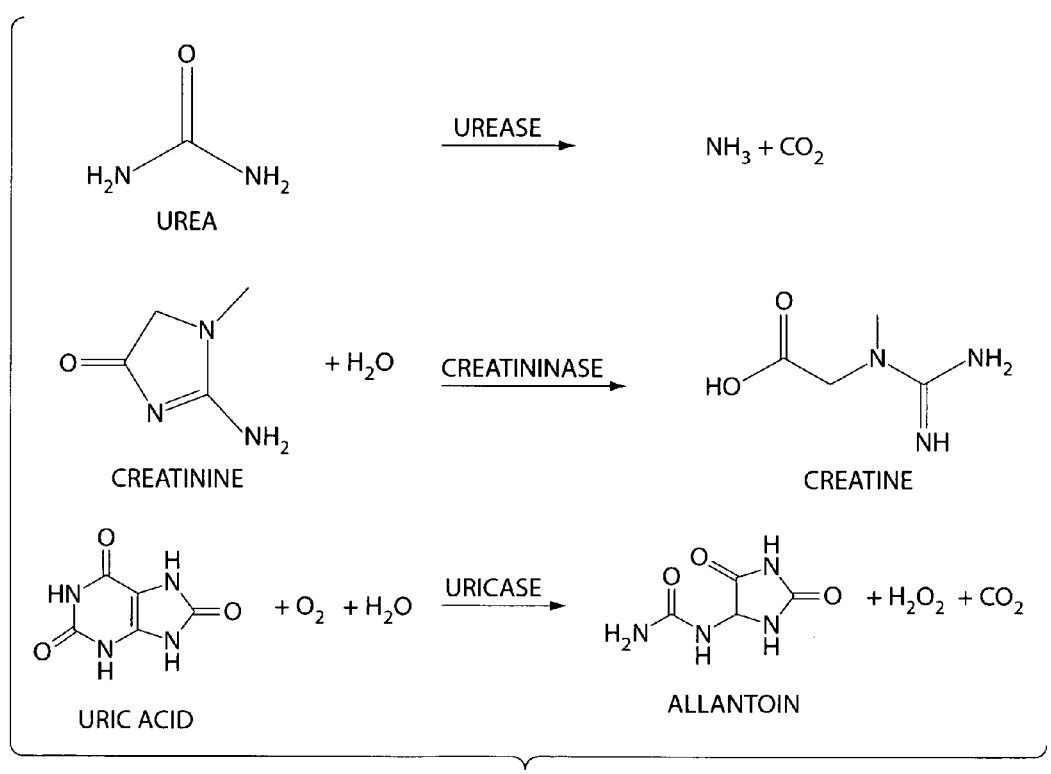
FIG. 1 illustrates certain enzymatic reactions of the invention.

The present invention generally relates to the treatment of disorders associated with uremic toxins in vivo using uremic toxin-treating enzymes, and/or cells capable of producing uremic toxin-treating enzymes or otherwise reacting with uremic toxins to reduce or eliminate the toxic activity of the uremic toxins. Non-limiting examples of (disorders associated with uremic toxins include renal disease or dysfunction, gout, subjects receiving chemotherapy, or the like. In one aspect, the treatment includes an oral delivery composition able to reduce the blood concentration of one or more non-protein nitrogen compounds in vivo. The composition, in some cases, may comprise one, two, or more uremic toxin-treating enzymes, such as urease, uricase or creatininase. The oral delivery composition may be able to deliver the uremic toxin-treating enzymes, substantially undigested, to the intestines, where the enzymes can interact with uremic toxins transported to the intestines from the bloodstream. In another aspect, the treatment includes an oral delivery composition comprising a cell able to reduce the concentration of one or more uremic toxins in vivo. In some cases, the cell may be designed to overexpress one, two, or more uremic toxin-treating enzymes, such as urease, uricase or creatininase, for example, by transfecting the cell with a corresponding gene. In some embodiments, a species able to react with or otherwise sequester by-products of the uremic toxin-treating enzyme reactions may be included with the oral delivery composition. For example, if the by-product is ammonium, the species may be a sorbent able to adsorb ammonium, an enzyme able to react with the ammonium, or the like.

The indefinite articles "a" and "an," as used herein in the specification and in the claims, unless clearly indicated to the contrary, should be understood to mean "at least one."

As used herein, "or" is understood to mean inclusively or, i.e., the inclusion of at least one, but including more than one, of a number or list of elements. Only terms clearly indicated to the contrary, such as "exclusively or" or "exactly one of," will refer to the inclusion of exactly one element of a number or list of elements.

The term "patient" or "subject" as used herein includes mammals such as humans, as well as non-human mammals such as non-human primates, cows, horses, pigs, sheep, goats, dogs, cats, rabbits, or rodents such as mice or rats.

As used herein, a "uremic toxin" is given its ordinary meaning as used in the art, e.g., one or more compounds containing nitrogen produced by the body as waste products, e.g., from the breakdown of proteins, nucleic acids, or the like. Typically, uremic toxins are not proteins. Non-limiting examples of uremic toxins include urea, uric acid, creatinine, and beta-2 ($\beta_2$) microglobulin (e.g., see FIG. 1). In healthy individuals, uremic toxins are usually excreted from the body through the urine. However, in certain individuals, uremic toxins are not removed from the body at a sufficiently fast rate, leading to uremic toxicity, i.e., a disease or condition characterized by elevated levels of at least one uremic toxin with respect to physiologically normal levels of the uremic toxin. Non-limiting examples of such diseases include renal disease or dysfunction, impaired or partial kidney function, gout, subjects receiving chemotherapy, or the like. Subjects receiving chemotherapy or other treatments may experience significant amounts of necrosis of cell populations, which can cause the releases of purines which are metabolized to uric acid. "Renal disease" includes early renal disease states (i.e., the kidneys do not perform at physiologically normal levels, but are able to process and remove some uremic toxins from the bloodstream), as well as end stage renal disease ("ESRD"), where the kidneys are substantially nonfunctional. Certain uremic toxins are transported between the bloodstream and the intestine, for example, urea, uric acid, or creatinine. As used herein, "transport" refers to any process in which a substance is moved from one location to another, for example, through diffusion (passive transport), facilitated diffusion, convection, transport proteins or other active transport systems, etc.

One aspect of the present invention involves delivering one, two, or more uremic toxin-treating enzymes to a subject, typically to the intestines. Preferably, the enzymes are delivered in a substantially undigested state. In some cases, one or more of the enzymes are isolated (e.g., as described below). As used herein, a "uremic toxin-treating enzyme," or a "uremic enzyme," is an enzyme able to react with a uremic toxin as a substrate, for example, the uremic toxic-treating enzyme may be an enzyme able to react with urea as a substrate, with uric acid as a substrate, or with creatinine as a substrate. Uremic enzymes can be determined in vitro, for example, by allowing the enzyme to react with a uremic toxin in solution and measuring a decrease in the concentration of the uremic toxin. Examples of uremic toxin-treating enzymes include, but are not limited to, ureases (which reacts with urea), uricases (which reacts with uric acid), or creatininases (which reacts with creatinine). FIG. 1 illustrates enzymatic reactions that typically occur with these enzymes. In some cases, each enzyme independently may originate from a different species (i.e., heterologous). In some cases, the enzyme is commercially available, for example, isolated and purified from other sources. A specific non-limiting example of a urease is urease from *Canavalia ensiformis*, having a sequence SEQ ID NO.: 1 (GenBank Accession number URJB GI:418642). A specific non-limiting example of a uricase is uricase from *Schizosaccharomyces pombe*, having a sequence SEQ ID NO.: 2 (GenBank Accession number T40869 GI:7493586). A specific non-limiting example of a creatininase is creatininase from *Arthrobacter* sp., having a sequence SEQ ID NO.: 3 (GenBank Accession number BAA25929.1 GI:3116224). Those of ordinary skill in the art will know of other suitable uremic toxin-treating enzymes. Additionally, minor changes to such enzymes (for example, through chemical changes or modifications, such as the addition of reporting groups, linkage to a physical surface, changes or substitutions in bases in the amino acid sequence of the enzyme, etc.) that do not alter the ability of the enzyme to recognize and react with its substrate are also included herein as uremic toxin-treating enzymes. For example, a urease, uricase, or creatininase may be covalently bound to a surface, for instance, in a microarray or an ELISA.

One or more uremic toxin-treating enzyme described herein may be isolated in certain cases. An "isolated" molecule (e.g., an enzyme), as used herein, is a molecule that is substantially pure and is free of other substances with which it is ordinarily found in nature or in vivo systems to an extent practical and appropriate for its intended use. For instance, the molecular species may be sufficiently pure or sufficiently free from substances such as biological constituents with which it is normally found in vivo so as to be useful in, for example, producing pharmaceutical preparations, or sequencing if the molecular species is a nucleic acid, peptide, enzyme, or polysaccharide. Because an isolated molecular species of the invention may be admixed with a pharmaceutically-acceptable carrier in a pharmaceutical preparation, and/or other physiologically-active agents (e.g., as described below), the molecular species may comprise only a small percentage by weight of the preparation. The molecular species is nonetheless substantially pure in that it has been substantially separated from the substances with which it may be associated in living systems. As examples, a uremic toxin-treating enzyme, such as urease, uricase, and/or creatininase may be associated with other molecules, such as a pharmaceutically acceptable carrier, a sorbent, a capsule (e.g., comprising alginate), etc.

Any suitable system or method may be used to orally deliver the uremic enzyme in a substantially undigested state. As used herein, an "oral delivery composition" is a composition that is designed to be delivered orally to a subject, i.e., the composition has been formulated in such a way that it is designed to be taken orally by a subject in a therapeutically effective amount without substantially adverse effects. For example, an enzyme may be delivered to a subject in an oral delivery composition that is a capsule, a sustained release pill, a controlled release formulation, a liposome, etc. As used herein, a "substantially undigested" enzyme (or other such substance) is an enzyme (or other substance) that enters the gastrointestinal system of a subject, and is not degraded or digested by the gastrointestinal system until at least reaching the site of delivery (e.g., the intestines), and/or is partially degraded or digested, but such that a therapeutically effective amount of the enzyme or other substance is able to reach the site of delivery. Degradation or digestion by the gastrointestinal system of the enzyme (or other substance) can occur, for example, through the action of pH, gastric acid, mechanical action, hydrolysis, digestive enzymes such as pepsin, trypsin, chymotrypsin, etc. In some cases, the enzyme is not degraded or digested by the gastrointestinal system and is excreted substantially intact.

In some cases, an enzyme is included in a formulation that is not substantially susceptible to degradation or digestion by the gastrointestinal system, i.e., a formulation that is able to deliver the enzyme to the site of delivery in a substantially undigested state. For example, the enzyme may be encapsulated in a formulation that resists degradation or digestion, the enzyme may be included in a formulation that is surrounded by a coating at least partially resistant to degradation or digestion, or the like. In certain instances, the formulation may be at least partially susceptible to degradation or digestion, but over time scales greater than the time it takes for the formulation to pass through the gastrointestinal system; thus, the formulation is still able to deliver the enzyme to the site of delivery in a substantially undigested state, even though some degradation or digestion of the enzyme may occur. As used herein, "substantially undigested state" refers to a level of degradation or digestion of the enzyme that does not impede the ability of the enzyme to recognize and react with its substrate. In some cases, it is preferred that the formulation be designed so as to not substantially release the uremic toxin-treating enzyme externally of the capsule, i.e., into the gastrointestinal system. That is, the formulation may be designed such that any release of the uremic toxin-treating enzyme externally of the capsule does not prevent the uremic toxin-treating enzyme remaining within the capsule from being able to react with uremic toxins found in the gastrointestinal system at a therapeutically effective rate.

In certain embodiments, the formulation may be chosen or designed to allow sufficient mass transport of uremic toxins into the formulation to occur such that the enzyme is able to react with uremic toxins found in the gastrointestinal system at a therapeutically effective rate. As used herein, "mass transport" is given its ordinary meaning as used in the art, i.e., the physical movement of a substance from location to another, using processes such as diffusion, convection, osmosis, etc. In some cases, the formulation can be designed such that it does not substantially impede mass transport of the uremic toxin into the formulation, i.e., where "substantially impede" refers to the ability of the uremic toxin to reach the site of the uremic toxin-treating enzyme without being significantly rate-limited, for example, such that the reaction of the uremic enzyme occurs over a time scale comparable to the time scale of mass transport of the uremic toxin from external the formulation to the enzyme. For example, a capsule and/or an enteric coating may allow diffusion to occur therethrough to a uremic enzyme at rates similar to rates of reaction of free enzyme to the uremic toxin.

In one set of embodiments, a formulation of the invention, such as a capsule, may contain one uremic toxin-treating enzyme, or more than one uremic toxin-treating enzyme (i.e., a "combination" formulation). More than one type of formulation may be given to a subject. For example, a subject may be given a first capsule containing a first enzyme and a second capsule containing a second enzyme, e.g., serially or simultaneously.

As one example, a formulation of the invention may contain one, two, or more uremic toxin-treating enzymes encapsulated within a capsule. The capsule may comprise alginate or other suitable polymers or materials able to at least partially resist degradation or digestion in the gastrointestinal system. Alginates are salts of alginic acid, a carbohydrate biopolymer that can be extracted from brown algae or other sources. Typically, alginates include monomers such as mannuronic acid or guluronic acid, although other monomers may be included as well. Other examples of suitable materials include lactic acid, glycolic acid, lysine, and hydroxyapatite, as well as mixtures or copolymers of these and/or other materials, e.g., poly(lactic-co-glycolic acid).

The capsules may be produced by any suitable technique known to those of ordinary skill in the art. For example, one or more uremic enzymes may be placed within a pre-polymeric solution that, upon solidification or polymerization, forms a capsule embedding the enzymes. Other compounds, such as sorbents, stabilizers, buffers, or the like may also be included within the capsule, e.g., as further described below. In some cases, post-processing steps may also be performed, for example, forming an enteric coating around the capsule.

As used herein, an "enteric coating" is given its ordinary meaning as used in the art, i.e., a coating that at least is partially resistant to degradation or digestion within the gastrointestinal system or at least a portion thereof, such as within the stomach. Those of ordinary skill in the art will know of suitable materials useful for enteric coatings. Non-limiting examples include enteric polymers such as cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer, etc. These may be used either alone or in combination, or together with other polymers than those mentioned above. The enteric coating may also include insoluble substances which are neither decomposed nor solubilized in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin, a diepoxybutane, etc. The enteric coating may also include starch and/or dextrin. In some embodiments, a formulation of the invention may include a species able to react with or otherwise sequester (isolate) one or more by-products of the uremic toxin-treating enzyme reactions. For example, in cases where ammonia ($NH_3$) is produced as a by-product, the species may react with or sequester ammonia, and that species may be referred to as an "ammonium uptake species." In some instances, the species may sequester the by-product through physical means, such as through physisorption mechanisms, i.e., by use of a sorbent such as zirconium phosphate, carbon, or oxystarch. In other instances, an enzyme able to react with a by-product may be used to react the by-products, for example, into a metabolically neutral form, into a form that can is useful (e.g., an amino acid), into a form that is non-toxic, etc. As an example, in cases where ammonia is produced as a by-product, an enzyme able to react with ammonia may be used, such as glutamine synthetase. As yet another example, a cell able to react with one or more by-products of the reaction may be included in the formulation. Also, combinations of such techniques may also be used in some cases, for example, a sorbent and an enzyme may be included in the capsule or other formulation.

Other active compounds may be added to the formulation as well, for example, other cells, enzymes, chemicals, drugs, reporting agents, etc. For example, bacteria and/or enzymes targeted toward other molecules elevated in uremia, such as beta-2 ($\beta_2$) microglobulin may be identified and added to the formulation. In another embodiment, bacteria capable of recycling ammonia into amino acid precursors may be used, which may, in some cases, counteract the malnutrition which often accompanies renal failure.

Another aspect of the invention involves using cells designed to overexpress a uremic toxin-treating enzyme. Such cells may be delivered to a subject in an oral delivery composition, such as those previously described (for example, encapsulated), optionally in combination with other cells, enzymes such as uremic toxin-treating enzymes, sorbents, or other species able to react with or otherwise sequester one or more reaction by-products, etc. As used herein, a cell that is "designed" to overexpress a uremic enzyme is intentionally chosen or selected to "overexpress" the uremic enzyme, i.e., to express the uremic enzyme at expression levels significantly greater than the expression level of the enzyme for that cell type (which can include zero or negligible expression levels). For example, such a cell may be artificially selected through natural selection processes to overexpress the uremic toxin-treating enzyme, the cells may be stimulated (e.g., with a hormone to overexpress the uremic toxin-treating enzyme, the cell may be transfected to overexpress the uremic toxin-treating enzyme, or the like.

The cell may be any cell able to overexpress the uremic enzyme at levels that are therapeutically effective. For example, the cell may be a bacterium or a mammalian cell. Bacteria may be advantages in some cases. For example, bacteria can grow and expand during their passage through the gastrointestinal system, thus increasing the effectiveness of this form of treatment. In some cases, the bacteria can metabolize some of the breakdown products from the enzymatic reaction, e.g., preventing their resorption. In certain cases, the bacteria efficiency (e.g. in terms of weight/degradation power) may be higher than that of isolated enzymes or encapsulated enzymes. Bacteria can also be relatively easy to grow quickly in large amounts, and are often less expensive than enzymes. Some bacteria can also metabolize uremic toxins intracellularly, such that the uremic enzymes stay well-protected from the environment of the gastrointestinal system. In one embodiment, the bacteria is not *E. coli*.

In some cases, the cell may be transfected, e.g., with one, two, or more genes for urease, uricase, creatininase, or other uremic toxin-treating enzymes. Those of ordinary skill in the art will know of suitable ways of transfecting cells. For example, some techniques for transformation (micro-injection, electroporation, calcium phosphate method, etc.) are described in Sambrook, et al., *Molecular Cloning: A Laboratory Manual*, Cold Spring Harbor Press, N.Y. (1989).

In one embodiment, a gene for urease, uricase, creatininase, or other uremic toxin-treating enzymes may be transfected into a cell using a DNA vector. The vector may be a vector in which the gene is functionally linked to one or more control sequences which allows expression of the corresponding enzymes. These include plasmids which can be replicated and/or expressed in prokaryotes or bacteria such as *E. coli* and/or in eukaryotic systems such as yeasts or mammalian cell lines.

Expression in prokaryotes may be carried out using techniques known in the art. The gene may be expressed as fusion proteins or as intact, native proteins. In some cases, fusion proteins may be produced in large quantities. The fusion proteins are generally more stable than the native polypeptide and are easy to purify. The expression of these fusion proteins can be controlled by normal host DNA sequences.

Producing intact native polypeptides using bacteria such as *E. coli* may require, in some cases, a strong, regulatable promoter and an effective ribosome binding site. Promoters which may be used for this purpose include, but are not limited to, the temperature sensitive bacteriophage $\lambda p_L$-promoter, the tac-promoter inducible with IPTG or the T7-promoter. Numerous plasmids with suitable promoter structures and efficient ribosome binding sites have been described, such as for example pKC30 ($\lambda p_L$; Shimatake and Rosenberg, *Nature*, 292:128 (1981), pKK173-3 (tac, Amann and Brosius, *Gene*, 40:183 (1985)) or pET-3 (T7-promoter (Studier and Moffat, *J. Mol. Biol.*, 189:113 (1986)). A number of other suitable vector systems for expressing the DNA according to the invention in bacteria are known from the prior art and are described, for example, in Sambrook, et al., *Molecular Cloning: A Laboratory Manual*, Cold Spring Harbor Press, N.Y. (1989).

Suitable bacterial strains which are specifically tailored to a particular expression vector are known to those skilled in the art (Sambrook, et al., *Molecular Cloning. A Laboratory Manual*, Cold Spring Harbor Press, N.Y. (1989)). The experimental performance of the cloning experiments, the expression of the polypeptides in bacteria and the working up and purification of the polypeptides are known.

In addition to prokaryotes, eukaryotic microorganisms such as yeast may also be used in some cases. For expression in yeast, the plasmid YRp7 (Stinchcomb et al. *Nature*, 282:39 (1979); Kingsman et al., *Gene* 7:141 (1979); Tschumper et al., *Gene*, 10:157 (1980)) and the plasmid YEp13 (Bwach et al., *Gene*, 8:121–133 (1979)) are used, for example. The plasmid YRp7 contains the TRP1-gene which provides a selection marker for a yeast mutant (e.g., ATCC No. 44076) which is incapable of growing in tryptophan-free medium. The presence of the TRP1 defect as a characteristic of the yeast strain used then constitutes an effective aid to detecting transformation when cultivation is carried out without tryptophan. The same is true with the plasmid YEp 13, which contains the yeast gene LEU-2, which can be used to complete a LEU-2-minus mutant.

Other suitable marker genes for yeast include, for example, the URA3- and HIS3-gene. Preferably, yeast hybrid vectors also contain a replication start and a marker gene for a bacterial host, so that the construction and cloning of the hybrid vectors and their precursors can be carried out in a bacterial host. Other expression control sequences suitable for expression in yeast include, for example, those of PHO3- or PHO5-gene.

Other suitable promoter sequences for yeast vectors contain the 5'-flanking region of the genes of ADH I (Ammerer, *Methods of Enzymology*, 101: 192–210 (1983)), 3-phosphoglycerate kinase (Hitzeman et al., *J. Biol. Chem.*, 255:2073 (1980)) or other glycolytic enzymes (Kawaski and Fraenkel, *Biochem. Biophys. Res. Comm.*, 108:1107–1112 (1982)) such as enolase, glycerinaldehyde-3-phosphate-dehydrogenase, hexokinase, pyruvate-decarboxylase, phosphofructokinase, glucose-6-phosphate isomerase, phosphoglucose-isomerase and glucokinase. When constructing suitable expression plasmids, the termination sequences associated with these genes may also be inserted in the expression vector at the 3'-end of the sequence to be expressed, in order to enable polyadenylation and termination of the mRNA.

Generally, any vector which contains a yeast-compatible promoter and origin replication and termination sequences is suitable. Thus, hybrid vectors which contain sequences homologous to the yeast 2μ plasmid DNA may also be used. Such hybrid vectors are incorporated by recombination within the cells of existing 2μ-plasmids or replicate autonomously.

The genetic constructs may generally contain one or more suitable regulatory elements (such as one or more suitable promoters, enhancers, terminators, etc.), 3'- or 5'-UTR sequences, leader sequences, selection markers, expression markers/reporter genes, and/or elements that may facilitate or increase (the efficiency of) transformation. These and other suitable elements for such genetic constructs will be clear to those of ordinary skill in the art, and may, for instance, depend upon the type of construct used, the intended host cell or host organism; the manner in which the nucleotide sequences of the invention of interest are to be expressed (e.g. via constitutive, transient or inducible expression); and/or the transformation technique to be used.

In some cases, one or more elements may be "operably linked" to the above-described genes and/or to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required. In some cases, the optional further elements of the genetic construct(s) used in the invention may be such that they are capable of providing their intended biological function in the intended host cell or host organism. For instance, a promoter, enhancer or terminator may be "operable" in the intended host cell or host organism, by which is meant that (for example) the promoter should be capable of initiating or otherwise controlling/regulating the transcription and/or the expression of a nucleotide sequence (e.g. a coding sequence) to which it is operably linked (as defined above). Such a promoter may be a constitutive promoter or an inducible promoter, and may also be such that it (only) provides for expression in a specific stage of development of the host cell or host organism, and/or such that it (only) provides for expression in a specific cell, tissue, organ or part of a multicellular host organism.

A selection marker may be chosen such that it allows (e.g., under appropriate selection conditions) host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence may be chosen such that, in the intended host cell or host organism, it allows for the desired post-translational modifications, and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism.

An expression marker or reporter gene may be chosen such that, in the host cell or host organism, it allows for detection of the expression of (a gene or nucleotide sequence present on) the genetic construct. An expression marker may optionally also allow for the localization of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence of the invention. Some preferred, but non-limiting examples include fluorescent proteins such as GFP.

The genetic constructs of the invention may generally be provided by suitably linking the nucleotide sequence(s) of the invention to the one or more further elements described above, for example using the techniques described in the general handbooks such as Sambrook et al., mentioned above.

Often, the genetic constructs will be obtained by inserting a nucleotide sequence in a suitable (expression) vector known per se. Some preferred, but non-limiting examples of suitable expression vectors include: vectors for expression in bacterial cells: pET vectors (Novagen) and pQE vectors (Qiagen); and vectors for expression in yeast or other fungal cells: pYES2 (Invitrogen) and Pichia expression vectors (Invitrogen).

The nucleotide sequences and/or genetic constructs may be used to transform a host cell. The host cell may be any suitable (prokaryotic or eukaryotic) cell or cell line, for example: a bacterial strain, including, but not limited to, *E. coli, Bacillus. Streptomyces* and *Pseudomonas*; and a yeast cell, including, but not limited to, *Kluyveromyces* or *Saccharomyces*.

In one aspect, a formulation of the invention may be used to control uremic toxins within the subject at an acceptable level. The formulation may be used to treat a subject having or at risk for uremic toxicity, as previously described. In some cases, the formulation may used independently. For example, a formulation of the invention may be given to a subject in lieu of dialysis, or before a subject has reached a state where dialysis is required. For instance, in a subject having or at risk for renal failure, a formulation of the invention may be given to the subject to control uremic toxin levels within the subject, to reduce the need for dialysis or other forms of treatment, etc. As another example, in a subject being treated using chemotherapy, a formulation of the invention may be given to the subject to control uremic toxin levels within the subject, for example, to prevent or at least control uremic toxicity symptoms, or to supplement normal kidney function. In other cases, the formulation may be used in combination with other treatments or strategies for controlling uremic toxins, such as dialysis, e.g., to supplement and/or enhance such treatments. For example, the formulation may be given simultaneously with dialysis, before and/or after dialysis, interspersed with dialysis, etc. For instance, on days where no dialysis is performed, a subject may be given a formulation of the invention, once a day, twice a day, once every other day, or at any other suitable frequency, for example, three times a week, four times a week, or five times a week. As a specific example, in a subject where dialysis is to be performed three times a week, a formulation of the invention may be given to the subject on the four days of the week where no dialysis is performed.

As one example, a formulation of the invention may be used in a subject as a replacement of dialysis (e.g., kidney dialysis), or as a supplement to dialysis. Those of ordinary skill in the art will be able to identify suitable types of dialysis. For example, in kidney dialysis, blood is typically pumped from a subject through a semiporous membrane that allows urea and salt transport across the membrane to occur, but does not allow passage of red blood cells, white blood cells, and other important blood components therethrough. Examples of dialysis techniques include hemodialysis and peritoneal dialysis, for instance, continuous ambulatory peritoneal dialysis ("CAPD"). Dialysis can be performed, for example, using external machines or portable devices. By supplying the subject with the compositions of the invention, the time between dialysis treatments may be extended in some cases. For instance, the subject may be able to prolong the time between dialysis treatments to at least three days, at least four days, at least five days, at least seven days, or at least ten days or more in some cases.

As another example, a formulation of the invention may be used in combination with other small-molecule drugs, and/or other enzymes such as urate oxidase. As yet another example, a formulation of the invention may be used in combination with treatments that allow inhibition of uric acid synthesis, increased uric acid excretion, and/or enzymatic degradation. For instance, for the treatment of gout, a form of inflammatory arthritis in which urate deposits are common in and around the joints and characterizable by elevated levels of uric acid in the blood, the most often used drugs include allopurinol and probenecid. Allopurinol can interfere with uric acid synthesis by inhibiting xanthine oxidase, an enzyme which is required in the formation of uric acid, and probenecid can increase uric acid excretion by inhibiting the reabsorption of urate in the renal tubules. Rasburicase, a form of recombinant urate oxidase cloned from *Aspergillus flavus* fungi, is an example of a treatment for chemotherapy-induced hyperuricaemia. This enzyme, which may be given by intravenous injection, can degrade the uric acid via conversion of uric acid to allantoin, which is 5–10 times more soluble than uric acid.

Another aspect of the present invention provides a method of orally administering any of the above-described formulations to a subject. After oral delivery, the formulation may stay within the gastrointestinal system until being eliminated by the subject, typically after roughly twenty-four hours after administration. The formulation may be active during part or all of its transit through the gastrointestinal system, for example, within the large and/or small intestine.

When administered, the formulations of the invention are applied in a therapeutically effective, pharmaceutically acceptable amount as a pharmaceutically acceptable formulation. As used herein, the term "pharmaceutically acceptable" is given its ordinary meaning. Pharmaceutically acceptable formulations are generally compatible with other materials of the formulation and are not generally deleterious to the subject. Any of the formulations of the present invention may be administered to the subject in a therapeutically effective dose. A "therapeutically effective" or an "effective" as used herein means that amount necessary to at least partially decrease the concentrations of one or more uremic toxins within the bloodstream of the subject. When administered to a subject, effective amounts will depend on the particular condition being treated and the desired outcome. A therapeutically effective dose may be determined by those of ordinary skill in the art, for instance, employing factors such as those further described below and using no more than routine experimentation.

In administering the formulations of the invention to a subject, dosing amounts, dosing schedules, routes of administration, and the like may be selected so as to affect known activities of these formulations. Dosages may be estimated based on the results of experimental models, optionally in combination with the results of assays of formulations of the present invention. Dosage may be adjusted appropriately to achieve desired drug levels, local or systemic, depending upon the mode of administration. The doses may be given in one or several administrations per day. In the event that the response of a particular subject is insufficient at such doses, even higher doses may be employed to the extent that subject tolerance permits. Multiple doses per day are also contemplated in some cases.

The dose of the formulations to the subject may be such that a therapeutically effective amount of the active compound (enzyme and/or cell, etc.) reaches the intestines of the subject. The dosage may be given in some cases at the maximum amount while avoiding or minimizing any potentially detrimental side effects within the subject. The dosage of the formulation that is actually administered is dependent upon factors such as the final concentration desired, the efficacy of the formulation, the longevity of the formulation within the subject, the timing of administration, the effect of concurrent treatments (e.g., as in a cocktail, or in conjunction with dialysis), etc. The dose delivered may also depend on conditions associated with the subject, and can vary from subject to subject in some cases. For example, the age, sex, weight, size, environment, physical conditions, or current state of health of the subject may also influence the dose required. Variations in dosing may occur between different individuals or even within the same individual on different days. It may be preferred that a maximum dose be used, that is, the highest safe dose according to sound medical judgment. Preferably, the dosage form is such that it does not substantially deleteriously affect the subject.

Formulations suitable for oral administration may be presented as discrete units such as hard or soft capsules, pills, cachettes, tablets, troches, or lozenges. Other oral formulations suitable for use with the invention include solutions or suspensions in aqueous or non-aqueous liquids such as a syrup, an elixir, or an emulsion. In another set of embodiments, the formulation may be used to fortify a food or a beverage.

In certain embodiments of the invention, a formulation can be combined with a suitable pharmaceutically acceptable carrier, for example, as incorporated into a liposome, incorporated into a polymer release system, or suspended in a liquid, e.g., in a dissolved form or a colloidal form. In general, pharmaceutically acceptable carriers suitable for use in the invention are well-known to those of ordinary skill in the art. As used herein, a "pharmaceutically acceptable carrier" refers to a non-toxic material that does not significantly interfere with the effectiveness of the biological activity of the active compound(s) to be administered (e.g., enzymes, cells, etc.), but is used as a formulation ingredient, for example, to stabilize or protect the active compound(s) within the formulation before use. The term "carrier" denotes an organic or inorganic ingredient, which may be natural or synthetic, with which one or more active compounds of the invention are combined to facilitate the application of the formulation. The carrier may be co-mingled or otherwise mixed with one or more enzymes and/or cells, and with each other, in a manner such that there is no interaction which would substantially impair the desired pharmaceutical efficacy. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

In some embodiments, the formulations of the invention include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or alginic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. Those of ordinary skill in the art will know of other suitable formulation ingredients, or will be able to ascertain such, using only routine experimentation.

Preparations include sterile aqueous or nonaqueous solutions, suspensions and emulsions Aqueous carriers include water, alcoholic/aqueous solutions, or emulsions or suspensions, including saline and buffered media. Preservatives and other additives may also be present such as, for example, antimicrobials, antioxidants, chelating agents and inert gases and the like. Those of skill in the art can readily determine the various parameters for preparing and formulating the formulations of the invention without resort to undue experimentation.

In some embodiments, the present invention includes the step of bringing a formulation of the invention into association or contact with a suitable carrier, which may constitute one or more accessory ingredients. The final formulations may be prepared by any suitable technique, for example, by uniformly and intimately bringing the formulation into association with a liquid carrier, a finely divided solid carrier or both, optionally with one or more formulation ingredients as previously described, and then, if necessary, shaping the product.

In some embodiments, the formulations of the present invention may be present as a pharmaceutically acceptable salt. The term "pharmaceutically acceptable salts" includes salts of the formulation, prepared in combination with, for example, acids or bases, depending on the particular compounds found within the formulation and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

The present invention also provides any of the above-mentioned formulations useful for the treatment of uremic toxins in a subject, optionally including instructions for use of the formulation for such treatments. That is, the kit can include a description of use of the formulation for participation in any biological or chemical mechanism disclosed herein associated with uremic toxicity. The kit can include a description of use of the formulations as discussed herein. The kit can also include instructions for use of a combination of two or more formulations of the invention. Instructions also may be provided for administering the drug by any suitable technique, as described above. A "kit," as used herein, defines a package including any one or a combination of the formulations of the invention, and/or homologs, analogs, derivatives, enantiomers and functionally equivalent formulations thereof, and may also include instructions of any form that are provided in connection with the formulation in a manner such that a clinical professional will clearly recognize that the instructions are to be associated with the specific formulation, for example, as described above. The kits described herein may also contain, in some cases, one or more containers, which can contain formulations such as those described above. The kits also may contain instructions for mixing, diluting, and/or administrating the formulation. The kits also can include other containers with one or more solvents, surfactants, preservative and/or diluents (e.g., normal saline (0.9% NaCl), or 5% dextrose) as well as containers for mixing, diluting or administering the formulation to the subject.

The formulations of the kit may be provided as any suitable form, for example, as liquid solutions or as dried powders. When the formulation provided is a dry powder, the formulation may be reconstituted by the addition of a suitable solvent, which may also be provided. In embodiments where liquid forms of the formulation are used, the liquid form may be concentrated or ready to use. The solvent will depend on the formulation and the mode of use or administration. Suitable solvents for drug formulations are well known and are available in the literature.

The kit, in one set of embodiments, may comprise a carrier that is compartmentalized to receive in close confinement one or more container means such as vials, tubes, and the like, each of the compartments comprising one of the separate elements to be used in the method. For example, one of the compartments may comprise a positive control for an assay. Additionally, the kit may include containers for other components of the formulations, for example, buffers useful in the assay.

The invention also involves, in some embodiments, the promotion of the treatment of uremic toxins in a subject according to any of the techniques and formulations described herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, replacing, or the like that can be associated with the methods and formulations of the invention, e.g., as discussed herein. Promoting may also include, in some cases, seeking approval from a government agency to sell a formulation of the invention for medicinal purposes. Methods of promotion can be performed by any party including, but not limited to, businesses (public or private), contractual or sub-contractual agencies, educational institutions such as colleges and universities, research institutions, hospitals or other clinical institutions, governmental agencies, etc. Promotional activities may include instructions or communications of any form (e.g., written, oral, and/or electronic communications, such as, but not limited to, e-mail, telephonic, facsimile, Internet, Web-based, etc.) that are clearly associated with the invention. As used herein, "instructions" can define a component of instructional utility (e.g., directions, guides, warnings, labels, notes, FAQs ("frequently asked questions"), etc., and typically involve written instructions on or associated with the formulation and/or with the packaging of the formulation, for example, use or administration of the formulation, e.g., in the treatment of uremic toxins in a subject. Instructions can also include instructional communications in any form (e.g., oral, electronic, digital, optical, visual, etc.), provided in any manner such that a user will clearly recognize that the instructions are to be associated with the formulation, e.g., as discussed herein.

The following examples are intended to illustrate certain aspects of certain embodiments of the present invention, but do not exemplify the full scope of the invention.

EXAMPLE 1

A uremic test solution containing metabolites at levels comparable to those found in the blood of ESRD patients was prepared. The solution included urea (100 mg/dl) (Fisher Scientific), uric acid (10 mg/dl) (Sigma), and creatinine (10 mg/dl) (Fluka), dissolved in saline. The enzymatic reduction of these metabolites was measured using spectrophotometric assay (using kits from Sigma), at 535 nm, 686 nm, and 555 nm respectively. All experiments were conducted at 37° C. The solutions were maintained in an orbital shaker, and samples were stored in a −80° C. freezer between collection and measurement, except for the final time point.

To evaluate the capacity of unencapsulated enzymes to degrade the uremic toxins in the test solution, an enzyme-containing solution was prepared. The enzyme-containing solution included 800 units (50 mg) of urease from jack beans (solid powder), 10 units (0.6 mg) of uricase from *Arthrobacter globiformis* (aqueous solution) and 40 units (0.14 mg) of creatininase (aqueous solution) from *Flavobacterium* (Sigma). The enzyme-containing solution was added to the test solution, and changes in the metabolite concentration were monitored by spectrophotometric assay. Samples were taken every 4 hours from 0 hours to 12 hours, and again at 24 hours. These experiments were performed in triplicate. Dose-response trials were also conducted, in which the concentrations of the enzymes in solution were reduced by 10-fold and 100-fold and evaluated under the same conditions. These experiments were performed in duplicate.

Figure 2A:
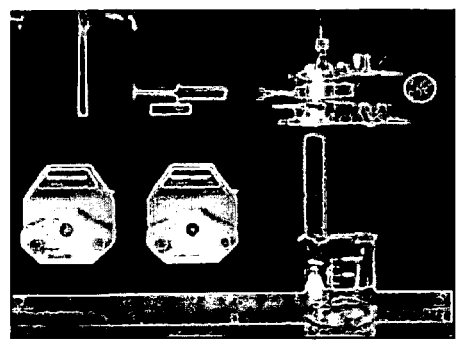
FIGS. 2A–2C are photocopies of photographs of alginate microspheres and systems used to produce them, in accordance with one embodiment of the invention.
Figure 2B:
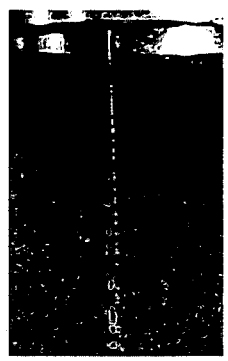
Figure 2C:
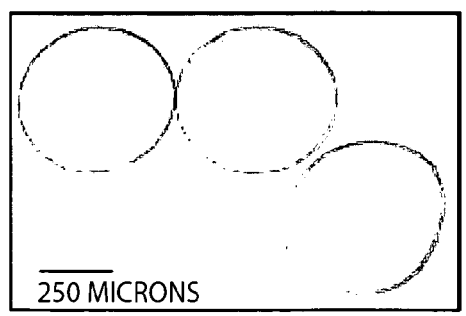
Figure 3:
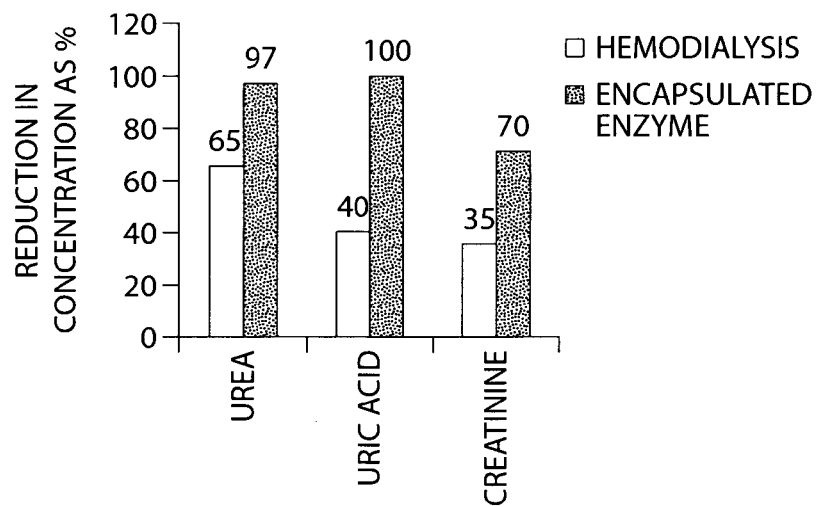
FIG. 3 illustrates the reduction in uremic toxins in 24 hours in an embodiment of the invention, compared to typical levels of reduction observed using clinical hemodialysis.

To evaluate the effectiveness of encapsulated enzymes, identical amounts of enzyme were utilized as in the unencapsulated trials (i.e., 800 units of urease, 10 units of uricase, and 40 units of creatininase), but the enzymes were mixed with 5 ml of 1.8% alginate solution (low viscosity alginic acid, Sigma); therefore, these in vitro experiments maintained a similar substrate-to-enzyme ratio for both unencapsulated and encapsulated enzymes. 5 ml of a mixture of alginate and enzymes was extruded through a 300 micrometer nozzle into a 1.4% calcium chloride bath (Sigma) to produce capsules containing encapsulated enzymes. All three enzymes were incorporated into each alginate capsule, thus forming a combination capsule, using an automated vibrational (f=1500 Hz) encapsulating method (Inotech). Alginate beads that were substantially spherical were produced (see FIG. 2C), which measured roughly 0.6 mm in diameter. The capsules were then added to 100 ml of uremic test solution, with an estimated dilutional effect of 5%. As in the unencapsulated trials, samples from the test solution were taken in duplicate at intermediate points every 4 hours from 0 hours to 12 hours, and finally at 24 hours. Each sample was tested for metabolite concentration by assay. This procedure was also repeated in triplicate, measuring metabolite concentration at 0 hours and 24 hours. In addition, as a control, in one set of experiments, empty alginate capsules were exposed to the uremic test solution.

Figure 4:
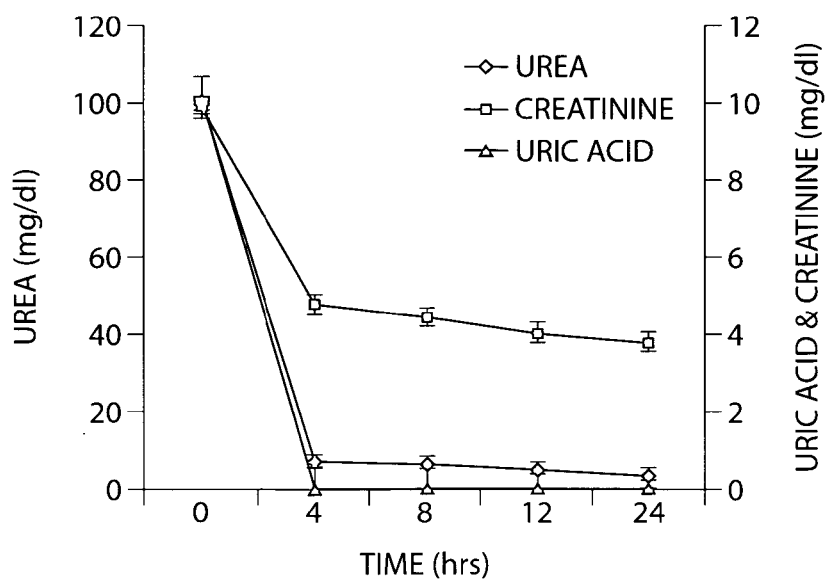
FIG. 4 illustrates the degradation of uremic toxins by encapsulated enzymes, according to one embodiment of the invention.
Figure 5A:
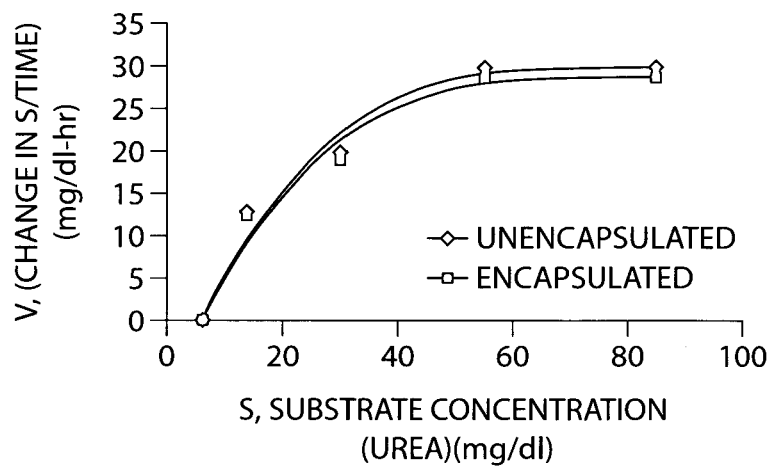
FIGS. 5A–5B illustrate urease degradation kinetics of an embodiment of the invention.

Results of these experiments showed that each enzyme effectively lowered its respective toxin in the uremic test solution, as shown in Table 1. In addition, the control (empty) capsules had the expected dilutional effect, based on the volume of alginate added to test solution, but did not otherwise show a detectable alteration in any of the uremic toxins in the test solution. Table 1 summarizes these results after 24 hours. The rate of metabolite degradation by each of the encapsulated enzymes to its respective toxin is shown in FIG. 4. This figure depicts the effectiveness of metabolite degradation by a system in which all three enzymes were present in capsules. FIG. 5A is based on Michaelis-Menten kinetics and shows the substrate concentration of urea versus the reaction velocity (change in concentration of urea with respect to time) for the action of unencapsulated and encapsulated urease on urea. The reaction velocity, V, was calculated as the change in the substrate concentration (urea in this case) over time, and plotted versus the substrate concentration, S, averaged over the measurement interval. The maximum velocity, $V_{max}$, and the Michaelis constant, $K_m$, for the enzyme (urease in this case) was then determined. In addition, the Michaelis-Menten equation was reformatted as a linear Lineweaver-Burk double reciprocal plot of 1/V vs. 1/S in FIG. 5B, where the expression $1/V_o$ was calculated as $(K_m/(V_{max}S))(1/V_{max})$.

TABLE 1

| | | Urea | Uric acid | Creatinine |
|---|---|---|---|---|
| Experiment #1 | Units of enzyme per 100 ml of test solution | 800 | 10 | 40 |
| | Number of trials | 5 | 5 | 5 |
| | Percent degradation in 24 hours | 95 ± 1 | >99 ± 0.2 | 59 ± 2 |
| Experiment #2 | Units of enzyme per 100 ml of test solution | 80 | 1 | 4 |
| | Number of trials | 2 | 1 | 2 |
| | Percent degradation in 24 hours | 13 ± 9 | 97 | 46 ± 13 |
| Experiment #3 | Units of enzyme per 100 ml of test solution | 8 | 0.1 | 0.4 |
| | Number of trials | 2 | 1 | 2 |
| | Percent degradation in 24 hours | 9 ± 3 | 40 | 19 ± 7 |

Table 1 shows that these experiments reproducibly demonstrated degradations of 95%, >99%, and 59%, respectively, for urea, uric acid, and creatinine, as observed over 24 hours. The degradation rates greatly decreased with dilution of enzyme quantity. For example, with a 100-fold reduced dose of enzyme, the amount of degradation was lowered to only 9%, 40%, and 19%, respectively, for urea, uric acid, and creatinine. In further experiments (data not shown), 5 ml of the encapsulated enzymes effectively degraded 97% of the urea, nearly 100% of the uric acid, and 70% of the creatinine within 24 hours in 100 ml of test solution. Thus, these results show that these uremic enzymes, in unencapsulated and encapsulated form, are able to efficiently degrade metabolites. Additionally, no substantial difference in efficacy between the unencapsulated and encapsulated enzyme was found.

Figure 5B:
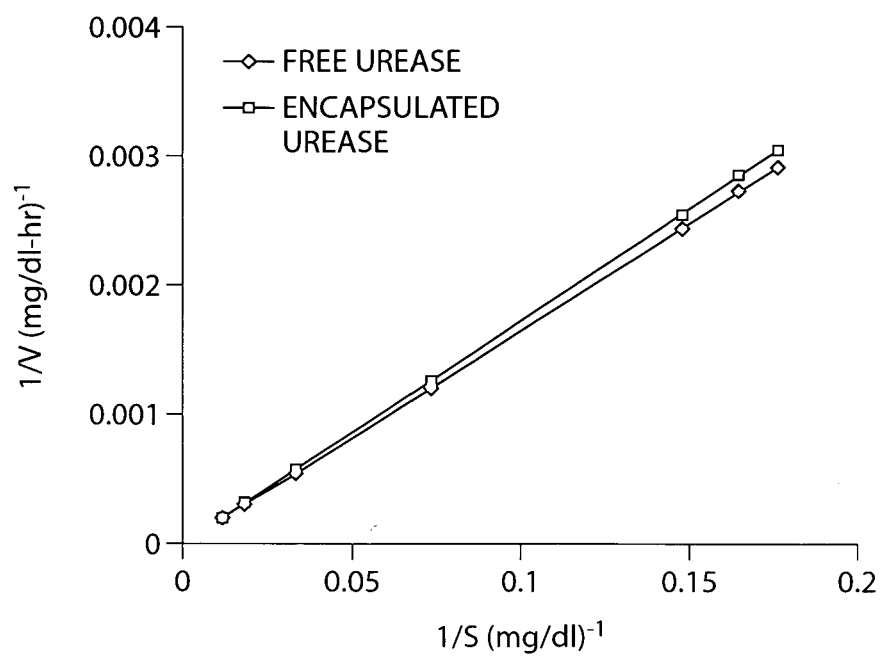
Figure 6A:
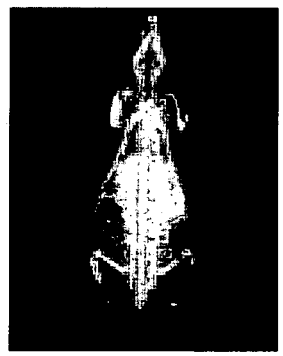
FIGS. 6A–6D illustrate the oral passage of an embodiment of the invention through a rat model.
Figure 6B:
Figure 6C:
Figure 6D:

FIG. 5B is a Lineweaver-Burk plot of the reciprocal of substrate concentration (urea in this case) versus the reciprocal of reaction velocity, as derived from the Michaelis-Menten equation. This figure demonstrates that the enzymatic behavior of urease that was observed was consistent with theory. This figure also shows that the observed urea degradation rates were nearly identical with both the encapsulated and unencapsulated enzymes, suggesting that the encapsulated enzymes are fully active within the capsules, and that mass transfer across the capsules is not a limiting factor.

These results may have important implications for a supplemental therapy, involving a treatment format employing an oral delivery composition (i.e., encapsulated) of enzymes for metabolite degradation. A typical uremic patient has a total body water volume of about 400 times what was employed in this example. Thus, if 400 times more enzyme were to be delivered, the quantity of enzymes would be approximately 2 g of urease, 0.2 g of uricase, and 0.6 g of creatininase, or just under 3 g of enzymes in total per day, a reasonable amount. Oral delivery composition of enzymes can thus serve as a supplement for an existing therapy, such as hemodialysis, or may be used independently, for example to delay the starting point of dialysis treatment for patients with at least some residual renal function and/or to prolong the time interval between dialysis sessions for current patients.

EXAMPLE 2

In this example, certain experiments, alginate capsules containing 30% barium sulfate (Mallinckrodt) by weight were fabricated for delivery into rats in an in vivo system. These capsules were otherwise identical to the capsules described previously in Example 1. Barium sulfate was added for X-ray visualization. Four Sprague-Dawley CD male rats weighing 250–300 g (Charles River Laboratories) were fed ~1 ml of the capsules mixed with maple syrup by oral gavage. Full body X-rays were taken at 0.5 hours, 2.5 hours, 4.5 hours, 6.5 hours, 10.5 hours, and 24 hours. The rats were briefly sedated for the X-ray photos with isoflurane gas, and were allowed free access to food and water throughout.

X-ray photographs of a rat, as shown in FIG. 6, show a widespread dispersion of barium sulfate capsules throughout the digestive system of the rat and a measurable residence time of at least 12 hours in the G1 tract. The X-ray photographs are from one rat, but are representative of the four rats X-rayed after oral delivery of the capsules.

A chemically-induced acute model of chronic renal failure was used in this in vivo study. Several other methods of inducing acute renal failure were investigated in this study including nephrectomy and the injection of mercuric chloride (data not shown). The chemically-induced renal failure model, based on intramuscular injection of glycerin, was chosen for this example due to its improved reliability and lack of technique dependence, compared to the other methods. Glycerol injection causes local tissue necrosis and the release of many soluble agents, and these agents accumulate in the kidney, leading to kidney failure. Capsule residence times were determined based on X-rays taken following oral administration of the barium-alginate capsules to the rats. As illustrated in FIG. 6, the initial bolus of capsules was well-separated in the digestive system of the rats, and the distribution of capsules reaches its maximum dispersion of up to about 6.5 hours after delivery. The capsules were still prominent at about 10.5 hours after gavage, but were located towards the caudal part of the gut. At 24 hours, no traces of the capsules could be seen. During the period the capsules were present in the intestine, they were able to adsorb and degrade toxins, including urea, uric acid, and creatinine. It was also shown that the capsules were able to pass through the digestive system without being substantially digested, i.e., the capsules were able to "escape" digestion.

EXAMPLE 3

In this example, following overnight water deprivation with free access to food, acute renal failure (ARF) was induced in cohorts of Sprague-Dawley CD male rats weighing 250–300 g (Charles River Laboratories) by intramuscular injection of hypertonic (50%) glycerol solution (glycerin, Mallinckrodt) at a dose of 10 ml/kg body weight, using methods similar to those described in Example 2. Plasma urea, uric acid, and creatinine levels were measured at time 0 hours, 1 hour, 3 hours, 5 hours, and 24 hours after injection, in both the lesioned rats and unlesioned control rats. Experiments were conducted on groups consisting of four rats, where three of the four received the injection, with one serving as a control. Blood samples were collected from the tail and placed in heparinized centrifuge tubes. The rats were briefly sedated during sample collection with isoflurane gas. After centrifugation, the samples were stored in the refrigerator and analyzed by assay after the final time point.

Lesioned rats and controls were fed capsules containing all three enzymes as described in the previous examples, in three cohorts of four rats each. All cohorts received identical glycerol injections. The first cohort received only the lesion, but no capsules. Encapsulated enzymes were delivered to the second cohort, and an oral sorbent (3 g/rat of ion exchange resin AG 50W-X8, Bio-Rad) was administered in conjunction with the capsules to the third cohort. In all instances of oral delivery, each rat received roughly 100 mg of encapsulated enzymes.

Each cohort of four rats was deprived of water overnight prior to glycerol injection. The capsules were administered immediately after glycerol injection. For oral delivery of the capsules, the rats were anesthetized using isoflurane gas, and microcapsules suspended in maple syrup were fed through an orogastric tube. The rats were subsequently allowed free access to food and water. The rats were again sedated for blood collection purposes taken via tail bleeding at time 0 hours, 1 hour, 3 hours, 5 hours, and 24 hours. The samples were collected in heparinized tubes, centrifuged, and the plasma analyzed to determine urea, uric acid, and creatinine concentrations by standard spectrophotometric assay. At the completion of the study, the rats were sacrificed in a $CO_2$ chamber. All animal experiments were conducted according to institutionally approved written protocols. The results are reported as mean±standard error (SEM). Statistical significance was evaluated using Student's t test.

Figure 7:
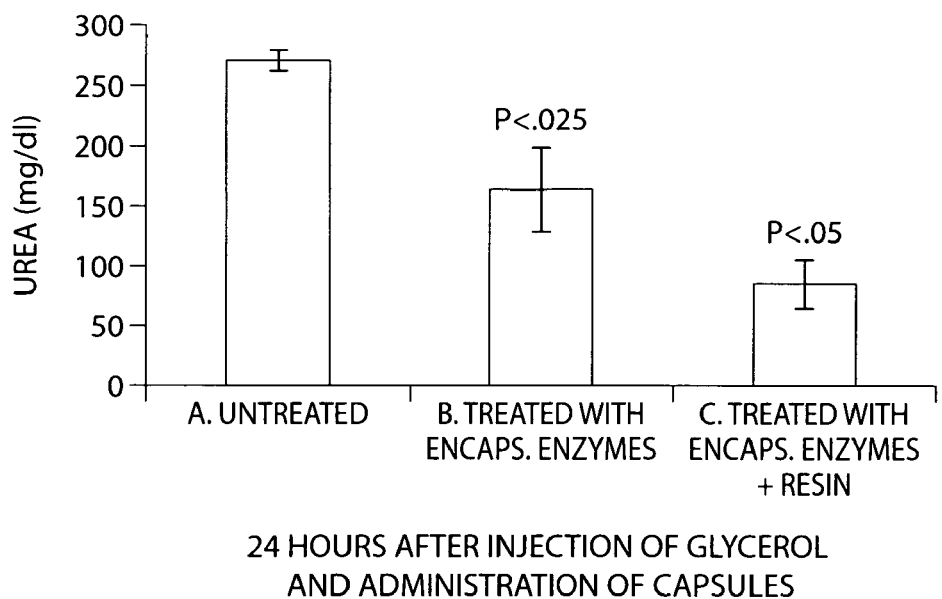
FIG. 7 illustrates the effect of sorbent on urea degradation, in accordance with one embodiment of the invention.

The results of these in vivo experiments are summarized in Table 2 and plotted for urea in FIG. 7. These experiments showed that acute renal failure was induced in the rats via intramuscular glycerol injection at a dose of 10 ml/kg. Over a period of 24 hours, measured concentrations rose by eightfold for urea, fifteen-fold for uric acid, and threefold for creatinine. Thus, as demonstrated in Table 2, the encapsulated enzyme therapy significantly decreased the magnitude of these metabolites within the bloodstreams of the rats.

TABLE 2

| | | Solute concentration 24 hours after lesion (mg/dl) | | |
|---|---|---|---|---|
| Treatment | N | Urea | Uric acid | Creatinine |
| Unlesioned controls | 4 | 35 ± 2 | 0.2 ± 0.3 | 1.4 ± 0.1 |
| Lesion only | 4 | 269 ± 9 | 3.3 ± 1 | 4.8 ± 0.9 |
| Lesion + encapsulated enzymes | 4 | 163 ± 35 | 0.8 ± 0.4 | 2.6 ± 0.2 |
| Lesion + encapsulated enzymes + ion exchange | 4 | 85 ± 20 | 0.8 ± 0.3 | 3.5 ± 0.7 |

Administration of the encapsulated enzymes along with an ion exchange resin sorbent decreased the severity of azotemia (i.e., the effect of elevated or toxic levels of urea and other uremic toxins) considerably. As shown in FIG. 7, rats receiving encapsulated enzyme therapy plus a sorbent displayed lower urea levels than those receiving only encapsulated enzymes, i.e., a 70% vs. a 40% decrease in urea concentration relative to lesioned but untreated cohort. The sorbent is believed to be beneficial to the rate of urea degradation, not for uric acid and creatinine, since ammonia is not formed from their degradation (see reactions in FIG. 1).

The results in FIG. 7 show that addition of an ion exchange resin, which serves as a sorbent able to remove high concentrations of ammonia in the GI tract, enhances the efficiency of urea removal. Urease degrades urea into ammonia and carbon dioxide and the ammonia needs to be removed, since it could potentially diffuse from the intestine to the liver and be converted back to urea. However, the resin is not required for degradation of uric acid and creatinine (as shown by the data in Table 2). Alternative approaches to ammonia uptake include metabolism to amino acids via glutamine synthetase, and/or the use of a sorbent, such as carbon, oxystarch, and zirconium phosphate.

Figure 8:
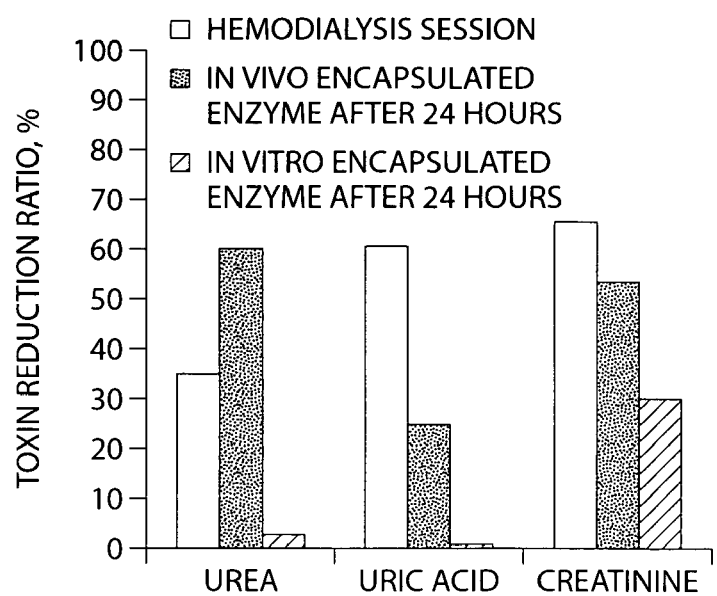
FIG. 8 illustrates a comparison of the effectiveness of one embodiment of the invention, as compared to the typical performance of clinical hemodialysis.

FIG. 8 shows a comparison of the amount of major uremic toxins remaining after one hemodialysis session, with encapsulated enzyme therapy in vitro (Example 1) and in vivo. This figure is useful as an assessment of what an embodiment of invention can remove in 24 hours verses clinically-accepted hemodialysis. On average, after a typical hemodialysis treatment, a subject retains about 35% of the predialysis urea; the corresponding numbers for uric acid and creatinine are about 60% and about 65%. In contrast, for the experiments described in Examples 1 and 3, the corresponding percentage retentions (relative to controls) were 3%, 0%, and 30%, respectively, for an in vitro, and, the percentage retention (relative to controls) was 60%, 25%, and 53% for an in vivo system.

EXAMPLE 4

In this example, microencapsulated enzymes and/or bacteria were orally administered which take up and degrade urea, uric acid, and creatinine while passing through the intestine. The targeted solutes are generated throughout the body, especially the liver, and diffuse into the capsules where they are degraded upon conversion of: 1) urea into ammonia and carbon dioxide, 2) uric acid into allantoin and hydrogen peroxide and 3) creatinine and water into creatine (see FIG. 1). The degradation products are excreted as waste.

This therapy may be useful in conjunction with hemodialysis to decrease the frequency and duration of treatments, and/or to provide improved outcomes for existing therapeutic regimens. In some cases, this treatment may allow a postponement of the initiation of dialysis in patients with early stage renal failure.

In this example, the development and characterization of a microcapsule containing a combination of both cells and enzymes is described, for instance, when a genetically modified cell expressing creatinine is not readily available. In some cases, the method of removing of non-protein nitrogen compounds can be combined with the removal of other solutes, such as beta-2 ($\beta_2$) microglobulin for which bacterial degradation may not be practical.

Enzymes purchased from a commercial source may be less complicated in terms of biocompatibility, immune reactions, and/or overall safety concerns. They may require much less effort in storage, packaging, and transportation and are likely to need less time to obtain FDA approval. However, bacteria can grow and expand during their passage through the gut and the bacteria may be able to metabolize some of the breakdown products from the enzymatic reaction in certain cases. Bacteria are readily available, since there are easy to grow quickly in large amounts, and less expensive than enzymes. Furthermore, bacteria may metabolize uremic compounds intracellularly, such that the metabolizing enzymes are protected from the external environment.

Genetically modified E. coli DH 5 cells expressing urease and E. Coli JM109 cells expressing uricase were prepared using techniques known to those of ordinary skill in the art. Luria-Bertani ("LB") growth medium was used for cell cultivation with a composition of 10 g/L sodium chloride (Sigma), 10 g/L tryptone, and 5 g/L yeast (Difco). The cell concentration was obtained by measurement of optical density at 600 nm according to the formula 1 Optical Density unit (O.D.)=$1\times10^6$ cells. Urease was obtained from jack beans, uricase from *Arthrobacter globiformis* and creatininase from *Flavobacterium* (all from Sigma).

A test solution consisting of metabolites at levels comparable to those found in the blood of kidney failure patients was prepared with urea (100 mg/dl) (Fisher Scientific), uric acid (20 mg/dl) (Sigma), and creatinine (10 mg/dl) (Fluka). Throughout, the reduction of the metabolites by the enzymes was measured by spectrophotometric assay (using kits from Sigma, 535, 686, and 555). All experiments were conducted at 37° C., solutions were maintained in an orbital shaker, and samples were stored in a −80° C. freezer between collection and measurement, except for the final time point.

For the kinetic experiments, 80 ml of each cell type were grown in LB medium along with ampicillin (1 mg/dl) overnight in a 37° C. orbital shaker. Just prior to capsule fabrication, the cell density was measured and the cells were centrifuged to form a pellet. Cells and enzyme were suspended in 5 ml of 1.8% alginate solution (low viscosity alginic acid, Sigma), loaded into a syringe and then extruded through a 300 micron diameter vibrational nozzle (frequency=1500 Hz), and formed into solid capsules upon contact with a 1.4% solution of calcium chloride (Sigma). This protocol, described in more detail in the previous examples, resulted in capsules with ~600 microns diameter. Each capsule contained known concentrations of the two bacteria types as well as the enzyme creatininase.

For in vitro studies, 5 ml of alginate capsules (approximately 50,000 capsules) containing 35 million urease cells, 20 million uricase cells and 40 units (0.14 mg) of creatininase were added to 100 ml of the test solution. 1 ml samples from the solution were taken at intermediate points every 4 hours from 0 hours to 12 hours and finally at 24 hours, and monitored for changes in metabolite concentration by assay. For dose response studies, the study was repeated but the quantities of cells were reduced to 40% and 10% of the amounts used in the initial experiments and the enzyme concentration was reduced by 10- and 100-fold.

For in vivo studies, three cohorts of rats received identical intramuscular glycerol injection at a dose of 10 ml/kg bodyweight of 50% solution to produce acute renal failure. The first group of four rats, received only the lesion but no capsules, thus serving as a measure of average solute concentration in this form of acute renal failure. The second group of two rats received an identical lesion, followed by administration of 2 ml of capsules (Table 3, Formulation A) containing a mixture of cells and enzymes, co-administered with cation exchange resin AG 50W-X8 (Bio-Rad). The third group of two rats received the lesion, followed by administration of 2 ml of capsules (Table 3, Formulation B) containing a mixture of cells and creatininase.

TABLE 3

| Quantity included per 2 ml dose (~20,000 capsules) | Formulation A | Formulation B |
|---|---|---|
| # of cells containing urease gene | 65 million | 65 million |
| # of cells containing uricase gene | 45 million | 45 million |
| Urease (units) | 1600 | — |
| Uricase (units) | 20 | — |
| Creatininase (units) | 60 | 60 |
| Ion exchange resin AG 50W-X8 | 3 g | — |

Except for the contents of the capsules, the overall procedure was similar to the procedure described in Example 3. Each cohort of rats was deprived of water overnight prior to glycerol injection. Capsules were administered immediately after glycerol injection. For oral delivery of the capsules, the rats were anesthetized using isoflurane gas and microcapsules suspended in maple syrup and fed through an orogastric tube. Rats were subsequently allowed free access to food and water. Rats were again sedated for blood collection. Small samples of 0.3 ml were collected from the tail at 0 hours, 1 hour, 3 hours, 5 hours and 24 hours for urea analysis. Larger samples of 0.7 ml were collected at 0 hours and 5 hours for determination of, uric acid, and creatinine concentration. All samples were collected in heparinized tubes, centrifuged, and the plasma analyzed by standard spectrophotometric methods. At the completion of the study, rats were sacrificed in a $CO_2$ chamber. All animal experiments were conducted according to institutionally-approved written protocols.

Figure 9A:
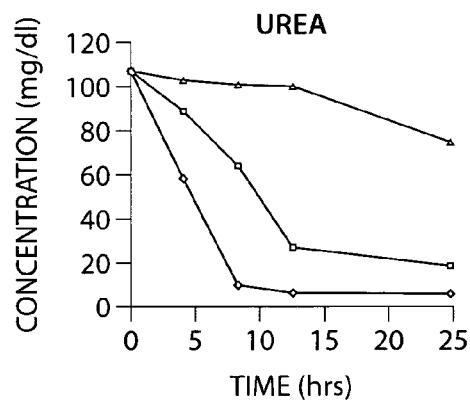
FIGS. 9A–9C illustrates the degradation in vitro of urea, uric acid, and creatinine using an embodiment of the invention.
Figure 9B:
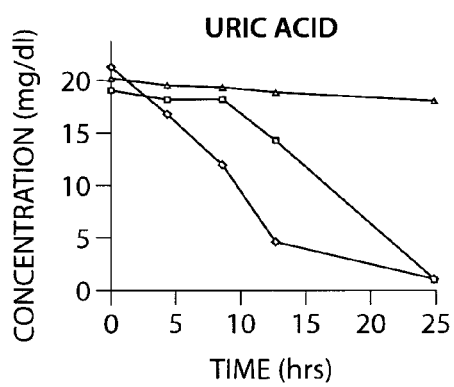
Figure 9C:
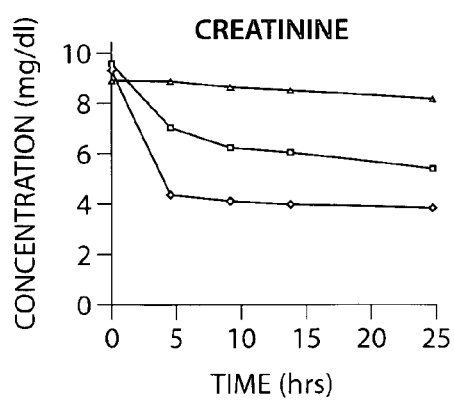

FIG. 9 demonstrates the rate of in vitro degradation of urea (FIG. 9A), uric acid (FIG. 9B), and creatinine (FIG. 9C) by encapsulated cells and enzyme exposed to the test solution for 24 hours. The concentration of the test solution is plotted versus time at varying capsule dosages. The graph demonstrates effectiveness of metabolite degradation by a system in which cells and enzymes were co-encapsulated. 5 ml of these capsules completely cleared >99% of the urea, 100% of the uric acid and 58% of the creatinine from 100 ml of a challenge solution formulated to model the concentration of these solutes in a hemodialysis patient.

In FIGS. 9A–9C, the standard dose, represented as diamonds, includes 5 ml of capsules (~50,000) containing an initial concentration of ~55 million cells (35 million *E. coli* DH5 and 20 million *E. coli* JM109 cells) and 40 units of creatininase (0.14 mg) added to 100 ml of test solution. Squares and triangles, respectively, represent 40% and 10% fewer cells and enzyme encapsulated in the same volume of alginate. These data are based upon single determinations. These figures demonstrate a clear dose response effect, with degradation rates decreasing with the quantity of cells and enzymes provided. The degradation rates appeared to decrease with dilution of cell and enzyme quantity.

Figure 10:
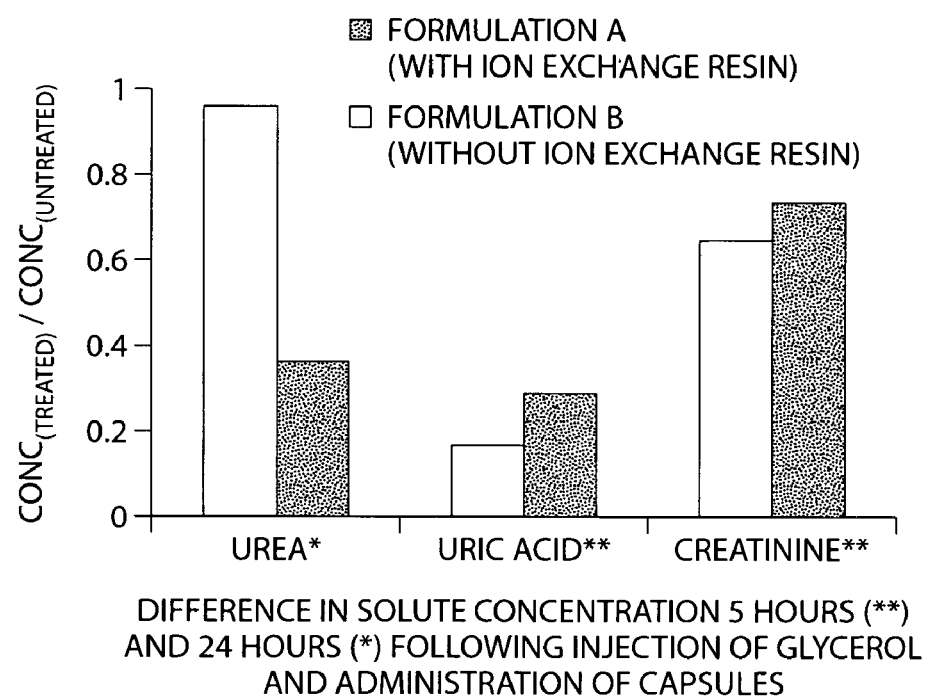
FIG. 10 illustrates the in vivo delivery of an embodiment of the invention.

In the in vivo trials with Wistar rats, orally administered capsules decreased the severity of azotemia, hyperuricemia and elevated creatinine following chemical induction of acute renal failure. FIG. 10 contains a bar graph plotting the ratio of solute concentration at different time intervals in animals receiving active capsules to unlesioned controls for two different capsule formulations. Both capsule formulations, described in Table 3, were highly effective for uric acid and creatinine degradation.

In FIG. 10, circulating urea, uric acid, and creatinine concentrations were each measured at 24 hours post lesion and capsule delivery for urea and 5 hours after for uric acid and creatinine. The results are reported as the ratio of concentration in treated rats to that in control rats. Two trials were performed: one with Formulation A (Table 3), in which the capsules contained cells and the enzymes urease, uricase, and creatininase as well as an ion exchange resin and the second with Formulation B (Table 3), in which the capsules contained only cells and creatininase. It was found that delivery of Formulation A generally decreases the severity of the hyperuricemic condition, lowers elevated creatinine after 5 hours, and reduces azotemia after 24 hours. The results after administration of Formulation B were similar for uric acid and creatinine at 5 hours and showed no effect on azotemia at 24 hours. The graph represents data from eight rats: four controls, and a total of four, two each in the two study groups.

These data thus show that in vivo, metabolite concentrations were lowered from the elevated levels following induction of acute renal failure. In addition, it was found that a cation exchange resin enhanced urea removal, while having no impact upon uric acid or creatinine removal. This is likely because free (unadsorbed) ammonia could diffuse from the intestine to the liver where it would be converted back to urea by a complex enzymatic pathway. However, the sorbent did not affect uric acid or creatinine degradation in this experiment, since ammonia was not a by-product of the enzymatic degradation of these compounds.

These data show that a combination of modified cells and enzymes, co-encapsulated in a single capsule and shown capable of efficiently degrading the most abundant uremic toxins (urea, uric acid, and creatinine) in vitro and lessening the elevation of the concentration of metabolites in vivo. This therapy format takes advantage of the intestinal tract as an effective route for the degradation of uremic waste. No apparent interference or blockage among the cells and enzymes was identified.

In the combination capsule described in this example, cells and enzymes displayed no synergistic or antagonistic effects. Creatininase was found to operate effectively in both the presence of enzymes and cells; the normal rise in creatinine following induction of renal failure was reduced by ~30%–45%. This method may thus be useful for the delivery of agents for which genetically modified cells are not available or difficult to create.

While several embodiments of the invention have been described and illustrated herein, those of ordinary skill in the art will readily envision a variety of other means and/or structures for performing the functions and/or obtaining the results and/or one or more of the advantages described herein, and each of such variations or modifications is deemed to be within the scope of the present invention. More generally, those skilled in the art will readily appreciate that all parameters, dimensions, materials, and configurations described herein are meant to be exemplary and that the actual parameters, dimensions, materials, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and/or claimed. The present invention is directed to each individual feature, system, material and/or method described herein. In addition, any combination of two or more such features, systems, articles, materials and/or methods, if such features, systems, articles, materials and/or methods are not mutually inconsistent, is included within the scope of the present invention.

All definitions as used herein are solely for the purposes of this disclosure. These definitions should not necessarily be imputed to other commonly-owned patents and/or patent applications, whether related or unrelated to this disclosure. The definitions, as used herein, should be understood to control over dictionary definitions, definitions in documents incorporated by reference, and/or ordinary meanings of the defined terms.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
an oral delivery composition, comprising a capsule and a pharmaceutically acceptable carrier, wherein the capsule comprises at least one cell transfected with both a uricase gene and a creatininase gene.

2. The article of claim 1, wherein the at least one cell is further transfected with a urease gene.

3. The article of claim 1, wherein the capsule, when ingested by a subject, does not substantially release the at least one cell externally of the capsule.

4. The article of claim 1, wherein the oral delivery composition comprises an ammonium uptake species.

5. An article, comprising:
an oral delivery composition, comprising a capsule and a pharmaceutically acceptable carrier, wherein the capsule comprises at least one cell transfected with each of a urease gene, a uricase gene, and a creatininase gene, wherein the at least one cell is not *E. coli*.

6. The article of claim 5, wherein the capsule, when ingested by a subject, does not substantially release the at least one cell externally of the capsule.

7. The article of claim 5, wherein the oral delivery composition comprises an ammonium uptake species.

* * * * *